United States Patent
Bader et al.

(10) Patent No.: US 11,028,104 B2
(45) Date of Patent: *Jun. 8, 2021

(54) XANTHINE DERIVATIVES, THEIR USE AS A MEDICAMENT, AND PHARMACEUTICAL PREPARATIONS COMPRISING THE SAME

(71) Applicants: MAX-DELBRÜCK-CENTRUM FÜR MOLEKULARE MEDIZIN, Berlin (DE); FORSCHUNGSVERBUND BERLIN E.V., Berlin (DE)

(72) Inventors: Michael Bader, Berlin (DE); Edgar Specker, Berlin (DE); Susann Matthes, Berlin (DE); Anja Schütz, Berlin (DE); Keven Mallow, Berlin (DE); Maik Grohmann, Eltville (DE); Marc Nazaré, Eltville (DE)

(73) Assignees: MAX-DELBRÜCK-CENTRUM FÜR MOLEKULARE MEDIZIN, Berlin (DE); FORSCHUNGSVERBUND BERLIN E.V., Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/867,835

(22) Filed: May 6, 2020

(65) Prior Publication Data
US 2020/0262847 A1    Aug. 20, 2020

Related U.S. Application Data

(63) Continuation of application No. 16/320,723, filed as application No. PCT/EP2017/068950 on Jul. 27, 2017, now Pat. No. 10,683,309.

(30) Foreign Application Priority Data

Jul. 28, 2016 (EP) .................. 16181667

(51) Int. Cl.
| | |
|---|---|
| A61P 1/12 | (2006.01) |
| A61P 3/00 | (2006.01) |
| A61P 11/00 | (2006.01) |
| A61P 19/00 | (2006.01) |
| A61P 25/00 | (2006.01) |
| A61P 35/00 | (2006.01) |
| C07D 519/00 | (2006.01) |

(52) U.S. Cl.
CPC .................. *C07D 519/00* (2013.01)

(58) Field of Classification Search
CPC .... A61P 1/12; A61P 3/00; A61P 11/00; A61P 19/00; A61P 25/00; A61P 35/00
See application file for complete search history.

(56) References Cited

U.S. PATENT DOCUMENTS

| | | |
|---|---|---|
| 10,214,530 B2 | 2/2019 | Bader et al. |
| 2009/0048280 A1 | 2/2009 | Burgoon, Jr. et al. |
| 2009/0088447 A1 | 4/2009 | Bednarz et al. |

FOREIGN PATENT DOCUMENTS

| | | |
|---|---|---|
| EP | 0 216 555 A2 | 4/1987 |
| EP | 0 219 555 A2 | 4/1987 |
| EP | 3 061 761 A1 | 8/2016 |
| WO | 2005/009343 A2 | 2/2005 |
| WO | 2010/003997 A1 | 1/2010 |
| WO | 2011/100285 A1 | 8/2011 |

OTHER PUBLICATIONS

Frandsen H. et al., "N-acetyltransferase-dependent activation of 2-hydroxyamino-1-methyl-6-phenylimidazo[4,5-b] pyridine: formation of 2-amino-1-methyl-6-(5-hydroxy)phenylumidazo[4,5-]pyridine, a possible biomaker for the reactive dose of 2-amino-1-methyl-6phenylimidazo[4,5-b]pyridine", Carcinogenesis, Oxford University Press, GB, vol. 21, No. 6. pp. 1197-1203, Jun. 2000.
Lei Zhang et al., "Discovery of Novel Vascular Endothelial Growth Factor Receptor 2 Inhibitors: A Virtual Screening Approach", Chemical Biology & Drug Design vol. 80, No. 6 pp. 893-901, Dec. 2012.
Extended European Search Report corresponds to European Application No. 161816673 dated Sep. 16, 2016.
International Search Report and Written Opinion dated Sep. 26, 2017.
Bader, M., "Inhibition of serotonin synthesis: A novel therapeutic paradigm," Pharmacology & Therapeutics, available at https://www.sciencedirect.com/science/article/pii/S0163725819301755?via%3Dihub (2019).
Choi et al., "Serotonin signals through a gut-liver axis to regulate hepatic steatosis," Nature Communication, pp. 1-9, (2018).

(Continued)

*Primary Examiner* — Bruck Kifle
(74) *Attorney, Agent, or Firm* — Norris McLaughlin, P.A.

(57) ABSTRACT

The invention relates to a xanthine derivative defined by chemical formula I or a salt thereof, its use as a medicament, especially for use in the treatment of serotonin-related diseases or disorders, and a pharmaceutical preparation comprising the xanthine derivative.

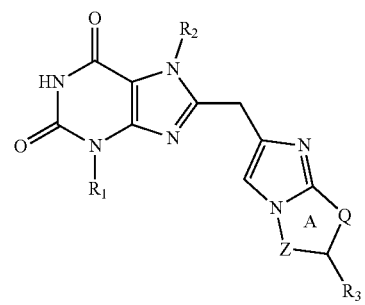

(I)

The novel xanthine compounds are capable of inhibiting tryptophan hydroxylases (TPH) involved in the biosynthesis of serotonin and are effective in influencing the serotonin level in the body.

11 Claims, No Drawings

(56) References Cited

OTHER PUBLICATIONS

Morecroft et al., "Effect of Tryptophan Hydroxylase 1 Deficiency on the Development of Hypoxia-Induced Pulmonary Hypertension," Hypertension, vol. 49, pp. 232-236, (2007).

Nowak et al., "Trytophan hydroxylase-1 regulates immune tolerance and inflammation," The Journal of Experimental Medicine, vol. 209, No. 11, pp. 2127-2135, (2012).

Pavel, M., "Telotristat Etiprate for Carcinoid Syndrome: A single-Arm, Multicenter Trial," J. clin. Endocrinol Metab, vol. 100, No. 4, pp. 1511-1519, Apr. 2015.

Rothman et al., "Altered Gene Expression in Pulmonary Tissue of Tryptophan Hydroxylase-1 Knockout Mice: Implications for Pulmonary Arterial Hypertension," PLoS ONE, vol. 6, No. 3, pp. 1-6, Mar. 2011.

U.S. Appl. No. 16/320,723, filed Jan. 25, 2019.

Oh et al., "Regulation of systemic energy homeostasis by serotonin in adipose tissues", Nature Comm., 2015, DOI 10.1038/ncomms7794.

Margolis et al., "Pharmacological reduction of mucosal but not neuronal serotonin opposes inflammation in mouse intestine", Gut, 2014, 63, 928-937.

Kim et al., "Blocking peripheral serotonin synthesis by telotristat etiprate (LX1032/LX1606) reduces severity of both chemical- and infection-induced intestinal inflammation", Am. J. Physiol. Gastrointest. Liver Physiol. 2015, 309, G455-G465.

Namkung et al., "Inhibition of Serotonin Synthesis Induces Negative Hepatic Lipid Balance", Diabetes Metab. J., 2018, 42, 233-243.

Wang et al., "Gut-Derived Serotonin Contributes to the Progression of Non-Alcoholic Steatohepatitis via the Liver HTR2A/ PPARγ2 Pathway", Front. Pharmacol., 2020, 11, Article 553.

Yadav et al., "Pharmacological inhibition of gut-derived serotonin synthesis is a potential bone anabolic treatment for osteoporosis", Nature Med. 16(3), 2010, 308-312.

Kulke et al., "Telotristat Ethyl, a Tryptophan Hydroxylase Inhibitor for the Treatment of Carcinoid Syndrome", J. Clin. Oncol., 2017, 35(1), 14-23.

Aiello et al., "Tryptophan hydroxylase 1 Inhibition Impacts Pulmonary Vascular Remodeling in Two Rat Models of Pulmonary Hypertension", J. Pharm. Experim. Therap., 2017, 360. 267-279.

Results of In Vivo Studies (TPH Inhibitor in Pulmonary Arterial Hypertension Model (2020)).

Crane et al., "Inhibiting peripheral serotonin synthesis reduces obesity and metabolic dysfunction by promoting brown adipose tissue thermogenesis", Nature Medicine, vol. 2, No. 21, Feb. 2015, 166-172.

XANTHINE DERIVATIVES, THEIR USE AS A MEDICAMENT, AND PHARMACEUTICAL PREPARATIONS COMPRISING THE SAME

This application is a continuation of U.S. patent application Ser. No. 16/320,723, filed Jan. 25, 2019, which is a § 371 national stage of PCT International Application No. PCT/EP2017/068950, filed Jul. 27, 2017, which claims foreign priority benefit under 35 U.S.C. § 119 of European Patent Application No. 16181667.3, filed Jul. 28, 2016, the entire disclosures of each of which are incorporated herein by reference.

The invention relates to novel xanthine derivatives effective in inhibiting tryptophan hydroxylases (TPH). The invention is further directed to the xanthine derivative for use as a medicament, particularly for use in the treatment of serotonin-related diseases and disorders, and pharmaceutical preparations comprising the xanthine derivative.

BACKGROUND OF THE INVENTION

Serotonin (5-hydroxytryptamine, 5-HT) is an evolutionary ancient biochemical, widespread throughout the animal and plant kingdoms. In mammals, serotonin acts as a neurotransmitter within the central and peripheral nervous systems (CNS, PNS) and as a local hormone in various other non-neuronal tissues, including the gastrointestinal tract, the cardiovascular system and immune cells. This functional duality of the serotonin system is typical for all vertebrates.

Within mammalian organisms only a few cell types synthesize serotonin, indicated by the expression of tryptophan hydroxylase (TPH) which is the initial and rate-limiting enzyme in the biosynthesis of serotonin. The multiplicity of serotonin actions is linked to many complex physiological and pathological functions. In mammals, about 70-90% of the total serotonin resides in the gastrointestinal tract, assisting digestive activities. There, it is mainly produced by enterochromaffin cells (EC) and by neurons of the enteric nervous system (ENS). Both cell types release serotonin upon mechanical or chemical stimuli, to induce contraction of smooth muscle cells and to regulate intestinal motility, secretion and intestinal blood flow. Serotonin from EC also enters the circulation and is taken up by thrombocytes and stored in specific vesicles. Platelet-derived serotonin plays a role in liver regeneration and primary haemostasis after vessel injury. Peripheral serotonin is also known to be involved in pulmonary hypertension, cardiac function, cardiac morphogenesis, ontogenesis, mammary gland plasticity, cancer, T-cell-mediated immune response and insulin secretion from pancreatic β-cells. The highest concentration of peripheral serotonin is found in the pineal gland, where it serves as precursor molecule for the biosynthesis of melatonin, a neuronal hormone involved in many physiological processes like thermoregulation and sleep.

Because of its hydrophilic properties, serotonin is not able to penetrate the blood-brain barrier (BBB). Therefore it needs to be synthesized in the brain, by serotonergic raphe neurons of the brainstem.

Central serotonin is important for the brain development. Furthermore, it is partaking in the regulation of sleep, body temperature, respiratory drive, motor control, CNS vascular tone, pain sensation and nociception. In addition, serotonin affects nearly all behavioural patterns, including memory, general mood, stress response, aggression, fear, appetite, addiction as well as maternal and sexual behaviour. An imbalance in the serotonin system has been implicated in a multitude of neuropsychiatric diseases.

The biosynthesis of serotonin is a highly regulated two-step process, starting with the essential amino acid L-tryptophan (Trp), cf. scheme below. The first and rate-limiting step comprises the hydroxylation of Trp to 5-hydroxytryptophan (5-HTP). This reaction is carried out by the enzyme tryptophan hydroxylase (TPH) and requires $Fe^{2+}$ ions as a cofactor and molecular oxygen ($O_2$) and tetrahydrobiopterin ($BH_4$) as co-substrates. Two isoforms of TPH (TPH1 and TPH2) exist, reflecting the functional duality of serotonin on the biochemical level. Secondly, 5-HTP is immediately decarboxylated to 5-hydroxytryptamine (5 HT) by the ubiquitously expressed aromatic amino acid decarboxylase (AAAD).

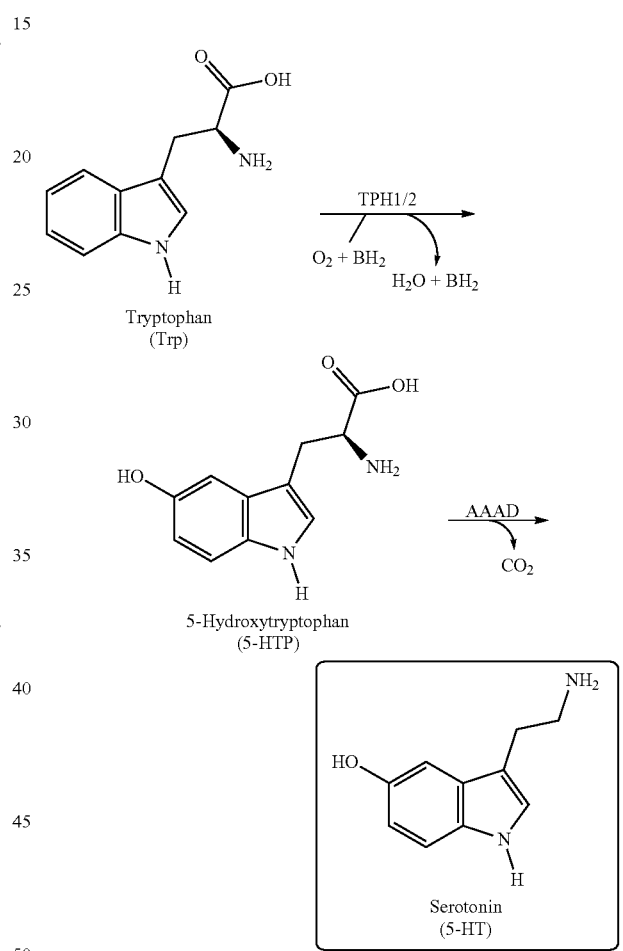

Biosynthesis of Serotonin (5-HT).

TPH1/2: Tryptophan hydroxylase 1 and 2, AAAD: Aromatic amino acid decarboxylase.

TPH1 and TPH2 proteins in vertebrates are highly homologous, sharing an overall 70% amino acid sequence identity in humans, but differ in their kinetic properties and, more remarkably, in their tissue distribution. Further studies of mRNA and protein levels in rodent and human tissues confirmed TPH2 to be the central isoform, predominantly expressed in raphe neurons of the brainstem and in peripheral myenteric neurons in the gut, while it is absent in peripheral organs, such as lung, heart, kidney or liver. On the other hand, TPH1 is mainly found in the gastrointestinal system as well as in the pineal gland, where it produces serotonin serving as a precursor molecule for melatonin biosynthesis.

The disability of serotonin to cross the BBB enforces the dualistic character of the serotonin system by creating two physiologically separated serotonin pools in the body. In fact, both serotonin systems are defined by the TPH1 and TPH2 isoforms and characterized by distinct physiological functions and independent regulatory mechanisms. Consequently, both systems can be targeted in an autonomous fashion to pharmacologically or genetically manipulate central and peripheral serotonin functions.

The catalytic domain of TPH is highly conserved and incorporates all of the residues required for enzyme activity and substrate binding. Data from X-ray structures of the catalytic domain helped to establish the structure of the active site and to reveal amino acid residues involved in substrate and cofactor binding. The carboxylate group of Trp interacts with $Arg^{257}$ and $Asp^{269}$, while the Trp side chain is held in a hydrophobic pocket formed by $Pro^{268}$, $His^{272}$, $Phe^{313}$ and $Phe^{318}$. The co-substrate $BH_4$ interacts with $Phe^{241}$ and $Glu^{273}$. Ligands to the non-heme iron ($Fe^{2+}$) are $His^{272}$, $His^{277}$ and $Glu^{317}$ are referred to as the 2-His-1-carboxylate facial triad. The general catalytic mechanism involves the iron-mediated incorporation of one atom of molecular oxygen into both the Trp substrate and the reducing co-substrate $BH_4$, yielding a hydroxylated product. This reaction is subdivided in three different steps, starting with the formation of an iron-peroxypterin and followed by its decay to a reactive intermediate and subsequent Trp hydroxylation via electrophilic aromatic substitution.

A variety of diseases are associated with a dysregulation of serotonin synthesis and metabolism. One example is carcinoid syndrome, a collection of symptoms resulting from an excessive release of hormones by carcinoid tumors. Carcinoid tumors develop from enterochromaffin cells, which produce serotonin, dopamine, tachykinins, and other substances that can have profound effects on the circulatory system, the gastrointestinal tract, and the lungs. Other serotonin-related cancer diseases comprise cholangiocarcinoma and neuroendocrine (N E) cancers, such as carcinoids and pancreatic endocrine tumors, prostate cancer.

A number of documents addresses compounds capable of influencing the serotonin level, in particular by inhibiting TPH (e.g. WO 2011/100285 A1, US 2009/0048280 A, WO 2010/003997 A1, US 2009/0088447 A1). The structures disclosed in WO 2011/100285 neither comprise a xanthine moiety nor a benzimidazolyl group.

However, because serotonin targets multiple receptors and is involved in so many biochemical processes, drugs that interfere with serotonin signalling are often attended by adverse effects. Thus, a need exists for new methods of affecting serotonin levels.

Lei Zhang et al. ("Discovery of Novel Vascular Endothelial Growth Factor Receptor 2 Inhibitors: A Virtual Screening Approach"; Chem. & Biol. Drug Des. 80 (2012), p. 893-901) disclose a benzimidazolyl xanthine derivative with potential use as inhibitor for vascular endothelial growth factor 2.

Henrik Frandsen et al. ("N-acetyltransferase-dependent activation of 2-hydroxyamino-1-methyl-6-phenylimidazo[4,5-b]pyridine: formation of 2-amino-1-methyl-6-(5-hydroxy)phenylimidazo[4,5-b]pyridine, a possible biomarker for the reactive dose of 2-amino-1-methyl-6-phenylimidazo[4,5-b]pyridine"; Carcinogenetics 21, 6 (2000), p. 1197-1203) describe a hydroxylated derivative of 2-amino-1-methyl-6-phenylimidazo[4,5-b]pyridine (PhIP) as a urinary biomarker for PhIP. PhIP is known to be a mutagenic and carcinogenic heterocyclic amine formed during frying of meat.

BRIEF DESCRIPTION OF THE INVENTION

The present invention, according to a first aspect, is directed to xanthine derivatives defined by chemical Formula I or a salt thereof:

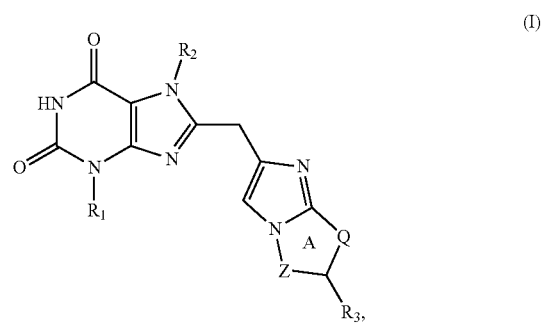

wherein $R^1$ and $R^2$ are each an optionally substituted group independently selected from hydrogen (—H), (C1-C10)-alkyl, (C2-C10)-alkenyl, (C2-C10)-alkynyl, (C5-C14)-aryl, (C5-C14)-heteroaryl, (C6-C15)-alkyl-arylene, (C6-C15)-alkyl-heteroarylene, (C6-C15)-alkenyl-arylene, (C6-C15)-alkenyl-heteroarylene, (C6-C15)-alkynyl-arylene, (C6-C15)-alkynyl-heteroarylene, (C6-C15)-aryl-alkylene, (C6-C15)-heteroaryl-alkylene, (C6-C15)-aryl-alkenylene, (C6-C15)-heteroaryl-alkenylene, (C6-C15)-aryl-alkynylene and (C6-C15)-heteroaryl-alkynylene, wherein the alkyl, alkenyl, alkynyl, alkylene, alkenylene, and alkynylene groups optionally comprise one or more bivalent groups substituting a carbon moiety in their hydrocarbon chain and selected from —O—, —S—, —S(O)—, —SO$_2$—, —N═, —N(R)—, —C(O)—, —C(O)O—, —OC(O)—, —C(O)N(R)—, —N(R)C(O)—, —OC(O)N(R)—, —N(R)C(O)O—, —N(R)C(O)N(R)—, (C3-C12)-heterocyclic alkylene and (C3-C12)-heterocyclic alkenylene;

$R^3$ is a group selected from hydrogen (—H), fluoro (—F), bromo (—Br), chloro (—Cl), hydroxyl (—OH), carbonyl (—C(O)R), carboxyl (—C(O)OH), carboxy ester (—CO$_2$R), alkoxy (—OR), aldehyde (—C(O)H), trihalide methyl ester (—OCX$_3$), primary, secondary and tertiary amine (—NR(R')), amide (—N(R)—C(O)—R), imide (—C(O)—N(R)—C(O)—R'), carbamate (—N(R)—C(O)—OR'), carboxamide (—C(O)N(R)R'), carbimide (—N(R)—C(O)—N(R')R''), primary and secondary ketimine (—(R)═NR'), secondary ketimine (—(R)═NH), nitrile (—CN), isonitrile (—NC), nitroxy (—ONO), nitro (—NO$_2$), nitrate (—ONO$_2$), nitroso (—NO), cyanate (—OCN), isocyanate (—NCO), sulfhydryl (—SH), sulfide (—SR), sulfurtrihalide (—SX$_3$), sulfurpentahalide (—SX$_5$), sulfinyl (—S(O)R), sulfonyl (—SO$_2$R), sulfino (—SO$_2$H), and sulfo (—SO$_3$H), and an optionally substituted and optionally linked group selected from (C1-C10)-alkyl, (C2-C10)-alkenyl, (C2-C10)-alkynyl, (C5-C14)-aryl, (C5-C14)-heteroaryl, (C6-C15)-alkyl-arylene, (C6-C15)-alkyl-heteroarylene, (C6-C15)-alkenyl-arylene, (C6-C15)-alkenyl-heteroarylene, (C6-C15)-alkynyl-arylene, (C6-C15)-alkynyl-heteroarylene, (C6-C15)- aryl-alkylene, (C6-C15)-heteroaryl-alkylene, (C6-C15)-aryl-alkenylene, (C6-C15)-heteroaryl-alkenylene, (C6-C15)-aryl-alkynylene and (C6-C15)-heteroaryl-alkynylene, wherein the alkyl, alkenyl, alkynyl, alkylene, alkenylene and alkynylene groups optionally comprise one or more bivalent groups substituting a carbon moiety in their hydrocarbon chain and selected from —O—, —S—, —S(O)—, —SO$_2$—, —N=, —N(R)—, —C(O)—, —C(O)O—, —OC(O)—, —C(O)N(R)—, —N(R)C(O)—, —OC(O)N(R)—, —N(R)C(O)O—, —N(R)C(O)N(R)—, (C3-C12)-heterocyclic alkylene or (C3-C12)-heterocyclic alkenylene;

Q is selected from carbon, nitrogen, oxygen, sulfur, —*CH$_2$—CH(R$^x$)—, —*CH=C(R$^x$)—, —*CH$_2$—O—, —*CH$_2$—N(R$^x$)—, wherein R$^x$ represents hydrogen, methyl, ethyl, cyclopropyl, or —CH$_2$— cyclopropyl, and wherein the carbon marked with an asterisk is covalently linked to the imidazole;

Z is selected from carbon (comprising hydrogenated and non-hydrogenated carbon), nitrogen (comprising hydrogenated and non-hydrogenated nitrogen), oxygen, and sulfur; and the ring member A is an saturated, unsaturated or aromatic ring;

wherein in the aforementioned definitions R, R' and R" independently mean hydrogen, (C1-C3)-alkyl or (C2-C3)-alkenyl.

The xanthine derivatives according to the present invention show a strong inhibiting effect of tryptophan hydroxylases TPH1 and/or TPH2 involved in the biosynthesis of serotonin. Thus, the xanthine derivatives according to the present invention can be used for the treatment of diseases or disorders, that are related to the level of serotonin in the human or animal body. In other words, the xanthine derivatives of the invention can be used to modulate the serotonin level in the body or in specific organs. Particular examples of the xanthine derivatives of the invention show a selective inhibition of TPH2 only. These compounds are thus suitable for the treatment of diseases related to the serotonin synthesized by cells or organs expressing TPH2. Other examples of the xanthine derivatives of the invention exhibit molecular properties which restrict their passage through the blood brain barrier. Because TPH2 is solely expressed in the brainstem these compounds are not able to target TPH2. Instead, these compounds are thus suitable for the treatment of diseases related to the serotonin synthesized by cells or organs expressing TPH1.

Another aspect of the present invention is directed to a xanthine derivative according to chemical Formula I as defined herein for use as a medicament.

Another aspect of the present invention is directed to a xanthine derivative according to chemical Formula I as defined herein for use in the treatment of serotonin-related diseases or serotonin-related disorders.

Another aspect of the present invention is directed to the use of a xanthine derivative according to chemical Formula I as defined herein in the treatment of serotonin-related diseases or disorders.

Yet another aspect of the present invention is directed to the use of a xanthine derivative according to chemical Formula I as defined herein in the manufacture of a medicament for the treatment of serotonin-related diseases or disorders.

Yet another aspect of the present invention is directed to a method of treatment of serotonin-related diseases or disorders, wherein the subject of need thereof is administered an effective amount of a xanthine derivative according to chemical Formula I as defined herein.

Another aspect of the present invention is directed to a pharmaceutical preparation comprising the xanthine derivative according to chemical Formula I as defined herein or a pharmaceutical acceptable salt thereof.

Serotonin-related diseases and disorders that can be treated with the xanthine derivatives according to the present invention comprise or consist of, for instance, TPH1-specific diseases and disorders:

Serotonin syndrome.

Bone diseases: osteoporosis, osteoporosis-pseudoglioma syndrome (OPPG), osteopenia, osteogenesis imperfecta, osteomalacia, renal osteodystrophy, faulty bone formation or resorption, Paget's disease, fractures and broken bones, bone metastasis.

Immunological diseases: systemic sclerosis, transplant rejection.

Pulmonary diseases: chronic obstructive pulmonary disease (COPD), pulmonary hypertension, asthma.

Gastrointestinal diseases: abdominal pain, carcinoid syndrome, celiac disease, constipation, Crohn's disease, diarrhea, emesis, anorectal disorders, bloating, dyspepsia, gallbladder disorders, irritable bowel syndrome, lactose intolerance, MEN types I and II, nausea, Ogilvie's syndrome, pancreatic insufficiency, somatization disorder, sphincter of Oddi disorders, ulcerative colitis, Zollinger-Ellison Syndrome.

Cancer: carcinoid tumours, pheochromocytoma, carcinoma of prostate, lung, bladder, intestine, breast, liver and ovary.

Vascular diseases: thrombosis, atherosclerosis, aortic aneurysm, coronary artery disease, peripheral artery disease, CREST syndrome (calcinosis, Raynaud's phenomenon, esophageal dysfunction, sclerodactyly), telangiectasia), migraine.

Inflammatory diseases: pancreatitis, hepatitis, asthma.

Metabolic diseases: non-alcoholic fatty liver disease, obesity, diabetes, metabolic syndrome.

Serotonin-related diseases and disorders that can be treated with the xanthine derivatives according to the present invention comprise or consist of, for instance, TPH2-specific diseases and disorders:

Psychiatric diseases: major depression, bipolar disorder, schizophrenia, hypoactive sexual desire disorder.

Accordingly, the xanthine derivative of Formula I according to the present invention may be used in the treatment of serotonin-related diseases or disorders comprising serotonin syndrome, osteoporosis, osteoporosis-pseudoglioma syndrome (OPPG), osteopenia, osteogenesis imperfecta, osteomalacia, renal osteodystrophy, faulty bone formation or resorption, Paget's disease, fractures and broken bones, bone metastasis; systemic sclerosis, transplant rejection; chronic obstructive pulmonary disease (COPD), pulmonary hypertension, asthma; abdominal pain, carcinoid syndrome, celiac disease, constipation, Crohn's disease, diarrhea, emesis, anorectal disorders, bloating, dyspepsia, gallbladder disorders, irritable bowel syndrome, lactose intolerance, MEN types I and II, nausea, Ogilvie's syndrome, pancreatic insufficiency, somatization disorder, sphincter of Oddi disorders, ulcerative colitis, Zollinger-Ellison Syndrome; carcinoid tumours, pheochromocytoma, carcinoma of prostate, lung, bladder, intestine, breast, liver and ovary; thrombosis, atherosclerosis, aortic aneurysm, coronary artery disease, peripheral artery disease, CREST syndrome (calcinosis, Raynaud's phenomenon, esophageal dysfunction, sclerodactyly), telangiectasia), migraine; pancreatitis, hepatitis, asthma; non-alcoholic fatty liver disease, obesity, diabetes, metabolic syndrome; major depression, bipolar disorder, schizophrenia and hypoactive sexual desire disorder.

According to specific embodiments, the xanthine derivative of the invention is used in the treatment of at least one of the following diseases or disorders selected from pulmonary hypertension, carcinoid syndrome, irritable bowel syndrome, thrombosis, osteoporosis, pancreatitis, hepatitis, non-alcoholic fatty liver disease, obesity, systemic sclerosis, transplant rejection, and major depression.

Xanthine Derivatives

Xanthine derivatives defined by chemical Formula I according to the present invention comprise any of their stereoisomeric forms, if any, and mixtures of stereoisomeric forms in any ratio.

The xanthine derivative may exist as a salt, preferably, a pharmaceutically acceptable salt. Pharmaceutically acceptable salts comprise inorganic acid salts such as chlorides, hydrochlorides, sulfates, bisulfates, nitrates, hydrobromides, hydroiodides and phosphates; organic carboxylates such as acetates, lactates, citrates, oxalates, glutarates, malates, tartrates, bitartrates, fumarates, mandelates, maleates, succinates, benzoates and phthalates; organic sulfonates such as methanesulfonates, ethansulfonates, benzenesulfonates, p-toluenesulfonates and camphor-sulfonates.

In Formula I, Q is selected from hydrogenated or non-hydrogenated carbon, hydrogenated or non-hydrogenated nitrogen, oxygen, sulfur, —*CH$_2$—CH(R$^x$)—, —*CH=C(R$^x$)—, —*CH$_2$—O—, —*CH$_2$—N(R$^x$)—, wherein R$^x$ represents hydrogen, methyl, ethyl, cyclopropyl, —CH$_2$-cyclopropyl, or a halogen. The carbon marked with an asterisk *C is directly covalently linked to the imidazole. If Q is selected from the two-membered groups —*CH$_2$—CH(R$^x$)—, —*CH=C(R$^x$)—, —*CH$_2$—O—, and —*CH$_2$—N(R$^x$)—, ring A will be a six-membered ring. Otherwise ring A is a five-membered ring.

According to preferred embodiments Q is ethylene —CH$_2$—CH$_2$—, ethenylene —CH=CH—, or sulfur —S—. Most preferably Q is sulfur.

In Formula I, Z is selected from carbon, nitrogen, oxygen and sulfur. Preferably Z is selected from carbon, including methylene —CH$_2$— and methenylene —CH=, and from nitrogen, including —NH— and —N=.

In particular preferred embodiments, Q is sulfur —S—, —CH=CH—, or —CH$_2$—CH$_2$— and Z is carbon or nitrogen.

Depending on the constitution of Q and Z, as to be substituted with H or R$^X$ or to be not substituted, the ring member A may be a saturated, an unsaturated or an aromatic ring.

In Formula I, R$^1$ bound to the nitrogen atom at position 3 of the xanthine moiety, is an optionally substituted group independently selected from hydrogen (—H), (C1-C10)-alkyl, (C2-C10)-alkenyl, (C2-C10)-alkynyl, (C5-C14)-aryl, (C5-C14)-heteroaryl, (C6-C15)-alkyl-arylene, (C6-C15)-alkyl-heteroarylene, (C6-C15)-alkenyl-arylene, (C6-C15)-alkenyl-heteroarylene, (C6-C15)-alkynyl-arylene, (C6-C15)-alkynyl-heteroarylene, (C6-C15)-aryl-alkylene, (C6-C15)-heteroaryl-alkylene, (C6-C15)-aryl-alkenylene, (C6-C15)-heteroaryl-alkenylene, (C6-C15)-aryl-alkynylene and (C6-C15)-heteroaryl-alkynylene, wherein the alkyl, alkenyl, alkynyl, alkylene, alkenylene and alkynylene groups optionally comprise one or more bivalent groups substituting a carbon moiety in their hydrocarbon chain and selected from —O—, —S—, —S(O)—, —SO$_2$—, —N=, —N(R)—, —C(O)—, —C(O)O—, —OC(O)—, —C(O)N(R)—, —N(R)C(O)—, —OC(O)N(R)—, —N(R)C(O)O—, —N(R)C(O)N(R)—, (C3-C12)-heterocyclic alkylene and (C3-C12)-heterocyclic alkenylene.

More specifically, R$^1$ may be an optionally substituted group independently selected from (C1-C7)-alkyl, (C2-C7)-alkenyl, (C2-C7)-alkynyl, (C5-C10)-aryl, (C5-C10)-heteroaryl, (C6-C10)-alkyl-arylene, (C6-C10)-alkyl-heteroarylene, (C6-C10)-alkenyl-arylene, (C6-C10)-alkenyl-heteroarylene, (C6-C10)-alkynyl-arylene, (C6-C10)-alkynyl-heteroarylene, (C6-C10)-aryl-alkylene, (C6-C10)-heteroaryl-alkylene, (C6-C10)-aryl-alkenylene, (C6-C10)-heteroaryl-alkenylene, (C6-C10)-aryl-alkynylene and (C6-C10)-heteroaryl-alkynylene, wherein the alkyl, alkenyl, alkynyl, alkylene, alkenylene and alkynylene groups optionally comprise one or more bivalent groups as defined above.

Particularly preferred bivalent groups for R$^1$ comprise —O—, —N(R)—, —C(O)—, —C(O)O—, —OC(O)—, (C3-C6)-heterocyclic alkylene and (C3-C6)-heterocyclic alkenylene.

According to particular embodiments, R$^1$ is selected from an optionally substituted linear, branched or cyclic (C1-C5)-alkyl group. According to specific examples R$^1$ is selected from the group consisting of methyl, ethyl, n-propyl, iso-propyl, cyclopropyl, cyclobutyl and cyclopentyl.

In Formula I, R$^2$ bound to the nitrogen atom at position 7 of the xanthine moiety, is optionally substituted group independently selected from hydrogen (—H), (C1-C10)-alkyl, (C2-C10)-alkenyl, (C2-C10)-alkynyl, (C5-C14)-aryl, (C5-C14)-heteroaryl, (C6-C15)-alkyl-arylene, (C6-C15)-alkyl-heteroarylene, (C6-C15)-alkenyl-arylene, (C6-C15)-alkenyl-heteroarylene, (C6-C15)-alkynyl-arylene, (C6-C15)-alkynyl-heteroarylene, (C6-C15)-aryl-alkylene, (C6-C15)-heteroaryl-alkylene, (C6-C15)-aryl-alkenylene, (C6-C15)-heteroaryl-alkenylene, (C6-C15)-aryl-alkynylene and (C6-C15)-heteroaryl-alkynylene, wherein the alkyl, alkenyl, alkynyl, alkylene, alkenylene and alkynylene groups optionally comprise one or more bivalent groups substituting a carbon moiety in their hydrocarbon chain and selected from —O—, —S—, —S(O)—, —SO$_2$—, —N=, —N(R)—, —C(O)—, —C(O)O—, —OC(O)—, —C(O)N(R)—, —N(R)C(O)—, —OC(O)N(R)—, —N(R)C(O)O—, —N(R)C(O)N(R)—, (C3-C12)-heterocyclic alkylene and (C3-C12)-heterocyclic alkenylene.

More specifically, R$^2$ may be an optionally substituted group independently selected from (C1-C7)-alkyl, (C2-C7)-alkenyl, (C2-C7)-alkynyl, (C5-C13)-aryl, (C5-C13)-heteroaryl, (C6-C13)-alkyl-arylene, (C6-C13)-alkyl-heteroarylene, (C6-C13)-alkenyl-arylene, (C6-C13)-alkenyl-heteroarylene, (C6-C13)-alkynyl-arylene, (C6-C13)-alkynyl-heteroarylene, (C6-C13)-aryl-alkylene, (C6-C13)-heteroaryl-alkylene, (C6-C13)-aryl-alkenylene, (C6-C13)-heteroaryl-alkenylene, (C6-C13)-aryl-alkynylene and (C6-C13)-heteroaryl-alkynylene, wherein the alkyl, alkenyl, alkynyl, alkylene, alkenylene and alkynylene groups optionally comprise one or more bivalent groups as defined above.

Preferably, R$^2$ comprises an aryl or a heteroaryl group.

Even more specifically, R$^2$ may be selected from an optionally substituted group selected from (C5-C13)-aryl, (C5-C13)-heteroaryl, (C6-C13)-alkyl-arylene, (C6-C13)-alkyl-heteroarylene, (C6-C13)-alkenyl-arylene, (C6-C13)-alkenyl-heteroarylene, (C6-C13)-alkynyl-arylene, (C6-C13)-alkynyl-heteroarylene, (C6-C13)-aryl-alkylene, (C6-C13)-heteroaryl-alkylene, (C6-C13)-aryl-alkenylene, (C6-C13)-heteroaryl-alkenylene, (C6-C13)-aryl-alkynylene and (C6-C13)-heteroaryl-alkynylene. According to an even more specific embodiment R$^2$ is selected from an optionally substituted (C6-C13)-aryl-alkylene and (C6-C13)-heteroaryl-alkylene.

Particularly preferred bivalent groups for $R^2$ comprise —O—, —N═, —N(R)—, —C(O)—, —C(O)O—, —OC(O)—, —C(O)N(R)—, —N(R)C(O)—, (C3-C6)-heterocyclic alkylene and (C3-C6)-heterocyclic alkenylene.

$R^2$ may be a group defined by chemical Formula Ia:

wherein $R^5$ is (C0-C3)-alkylene, preferably methylene —CH$_2$—, and Ar is an optionally substituted (C5-C12)-aryl or (C5-C12)-heteroaryl.

In Formula Ia, Ar is preferably (C5-C12)-aryl or (C5-C12)-heteroaryl. Preferably Ar comprises a monocyclic or bicylic aromatic moiety, wherein in case of a bicyclic aromatic moiety the two ring may be annealed or coupled via a bond. Particular preferred groups are selected from phenyl, pyrrole, pyrazole, imidazole, triazole, tretazole, pentazole, furane, such as furan-2-yl or furan-3-yl; oxazole, such as 1,3-oxazole-2-yl or 1,3-oxazole-5-yl; isoxazole (=1,2-oxazole), such as 1,2-oxazole-3-yl, 1,2-oxazole-4-yl or 1,2-oxazole-5-yl; oxadiazole, such as 1,3,4-oxadiazole-2-yl or 1,2,4-oxadiazole-3-yl; thiophene, such as thiophene-2-yl or thiophene-3-yl; thiazole, such as 1,3-thiazole-2-yl or 1,3-thiatole-5-yl; isothiazole (=1,2-thiazole), such as 1,2-thiazole-3-yl, 1,2-thiozole-4-yl or 1,2-thiazole-5-yl; thiadiazole, such as 1,2,4-thiadiazole or 1,3,4-thiadiazole, pyridine, 1,2-diazine, 1,3-diazine (pyrimidine), 1,4-diazine (pyrazine), 1,2,3-trazine, 1,2,4-trazine, 1,3,5-triazine, 1,2,3,4-tetrazine, 1,2,3,5-tetrazine, 1,2,4,5-tetrazine and their bicyclic combinations.

Preferred substituents of group Ar in Formula Ia comprise (C1-C3)-akyl, a primary, secondary or tertiary amino group —N(R)R' such as —NH$_2$, an amide group —NH—C(O)—R, such as acetamide —NH—C(O)CH$_3$, and a (C5-C6)-heterocyclic group, such as morpholino, in particular morpholin-4-yl.

Further in Formula Ia, $R^5$ is preferably a methylene group —CH$_2$—.

$R^2$ is may be an optionally substituted (C5-C6)-arylmethylene or (C5-C6)-heteroaryl-methylene, where the (C5-C6)-(hetero)aryl group is selected from those mentioned above. This is especially advantageous when selective inhibition of TPH2 is desired.

According to a specific embodiment, optionally substituted benzyl —CH$_2$—C$_6$H$_5$ is particular preferred as group $R^2$. In many cases, unsubstituted benzyl may be used as $R^2$. However, in some cases a substituted benzyl is used.

According to other specific embodiments, $R^2$ is —CH$_2$-phenylene-(C5-C6)-heteroaryl, with the (C5-C6)-heteroaryl group being selected from those mentioned for Ar in formula (Ia).

Preferred substituents of $R^2$, in particular for benzyl, comprise a (C1-C3)-alkyl group, a primary, secondary or tertiary amino group —N(R)R' such as —NH$_2$, an amide group —NH—C(O)—R, such as acetamide —NH—C(O)CH$_3$, and a (C5-C6)-heterocyclic group, such as morpholino, in particular morpholin-4-yl.

According to a preferred embodiment, at least one of $R^1$ and $R^2$ in Formula I is not hydrogen; even more preferred both of $R^1$ and $R^2$ are not hydrogen.

In Formula I, $R^3$ means a number of n groups independently selected from hydrogen (—H), fluoro (—F), bromo (—Br), chloro (—Cl), hydroxyl (—OH), carbonyl (—C(O)R), carboxyl (—C(O)OH), carboxy ester (—CO$_2$R), alkoxy (—OR), aldehyde (—C(O)H), trihalide methyl ester (—OCX$_3$), primary, secondary and tertiary amine (—NR(R')), amide (—N(R)—C(O)—R), imide (—C(O)—N(R)—C(O)—R'), carbamate (—N(R)—C(O)—OR'), carboxamide (—C(O)N(R)R'), carbimide (—N(R)—C(O)—N(R')R''), primary and secondary ketimine (—(R)═NR'), secondary ketimine (—(R)═NH), nitrile (—CN), isonitrile (—NC), nitroxy (—ONO), nitro (—NO$_2$), nitrate (—ONO$_2$), nitroso (—NO), cyanate (—OCN), isocyanate (—NCO), sulfhydryl (—SH), sulfide (—SR), sulfurtrihalide (—SX$_3$), sulfurpentahalide (—SX$_5$), sulfinyl (—S(O)R), sulfonyl (—SO$_2$R), sulfino (—SO$_2$H), and sulfo (—SO$_3$H), and an optionally substituted and optionally linked group selected from (C1-C10)-alkyl, (C2-C10)-alkenyl, (C2-C10)-alkynyl, (C5-C14)-aryl, (C5-C14)-heteroaryl, (C6-C15)-alkyl-arylene, (C6-C15)-alkyl-heteroarylene, (C6-C15)-alkenyl-arylene, (C6-C15)-alkenyl-heteroarylene (C6-C15)-alkynyl-arylene, (C6-C15)-alkynyl-heteroarylene, (C6-C15)-aryl-alkylene, (C6-C15)-heteroaryl-alkylene, (C6-C15)-aryl-alkenylene, (C6-C15)-heteroaryl-alkenylene, (C6-C15)-aryl-alkynylene and (C6-C15)-heteroaryl-alkynylene, wherein the alkyl, alkenyl, alkynyl, alkylene, alkenylene and alkynylene groups optionally comprise one or more bivalent groups as mentioned above.

In Formula I, $R^3$ is preferably selected from hydrogen, fluorine, chlorine, bromine, amine, amide, carbonitrile, sulfonic acid, carboxylic acid, carboxy ester, optionally substituted (C1-C10)-alkyl, including optionally substituted (C3-C10)-cycloalkyl, optionally substituted saturated or unsaturated (C5-C6)-heterocyclic, optionally substituted (C2-C10)-alkenyl, optionally substituted (C1-C5)-alkoxy, wherein the alkyl, cycloalkyl and alkenyl groups optionally comprise one or more bivalent groups as defined above.

Particularly preferred bivalent groups for $R^3$ comprise oxygen —O—, amine —N(R)— or —NH—, amide —N(R)—C(O)— or —NH—C(O)—.

Particularly preferred optionally substituted (C1-C10)-alkyl groups for $R^3$ comprise (C1-C3)-alkyl groups, including methyl, ethyl, isopropyl, and n-propyl.

Particularly preferred optionally substituted (C3-C10)-cycloalkyl groups for $R^3$ comprise (C3-C6)-cycloalkyl groups, including cyclopropyl, cyclopentyl and cyclohexyl.

Particularly preferred optionally substituted (C5-C6)-heterocyclic groups for $R^3$ comprise piperidine, such as piperidine-1-yl; piperazin, such as piperazin-1-yl or 4-(C1-C3)-alkyl-piperazin; morpholine, such as morpholine-4-yl.

Particularly preferred optionally substituted (C1-C5)-alkoxy groups for $R^3$ comprise methoxy, ethoxy, n-propyloxy, isopropyloxy and 2-hydroxyethoxy.

According to a specific embodiment, $R^3$ is hydrogen.

Particular preferred xanthine derivatives according to the invention comprise the following compounds according to chemical Formulas (I-1) to (I-39):

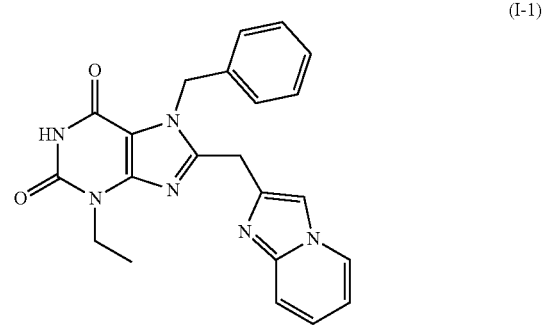 [SMILES: CCn1c(=O)[nH]c(=O)c2c1nc(Cc1cn3ccccc3n1)n2Cc1ccccc1]

(I-1)

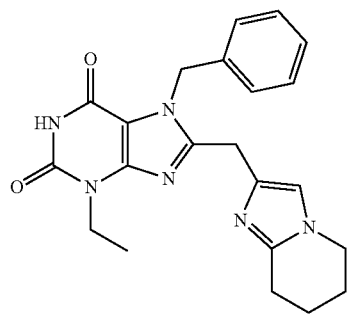
(I-2)
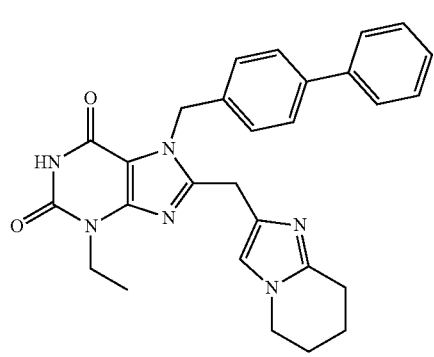
(I-3)
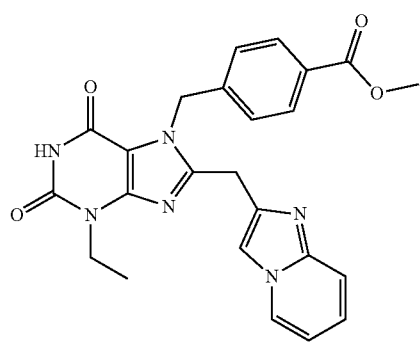
(I-4)
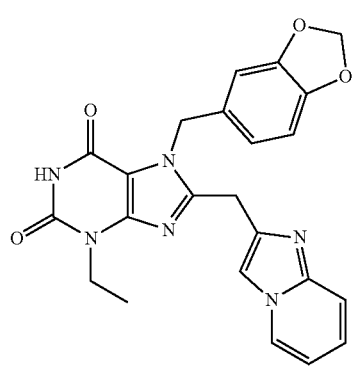
(I-5)
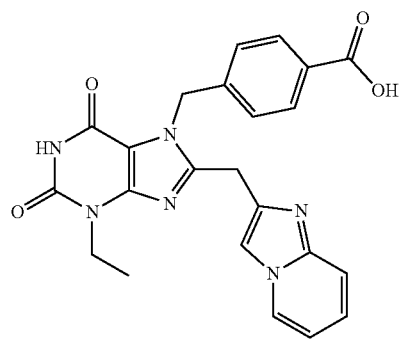
(I-6)
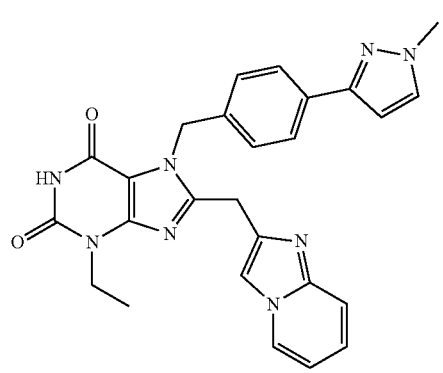
(I-7)
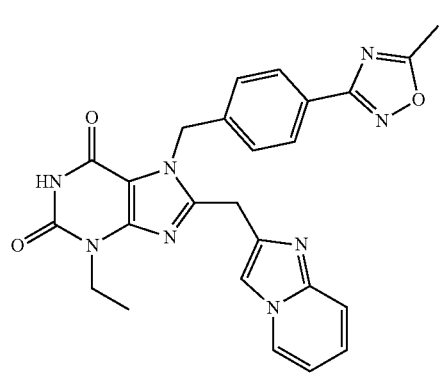
(I-8)
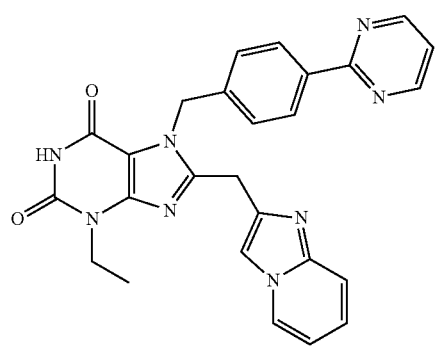
(I-9)

(I-10)
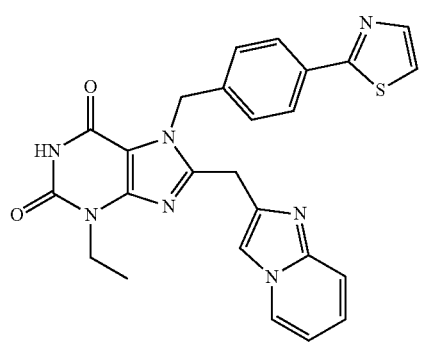
(I-11)
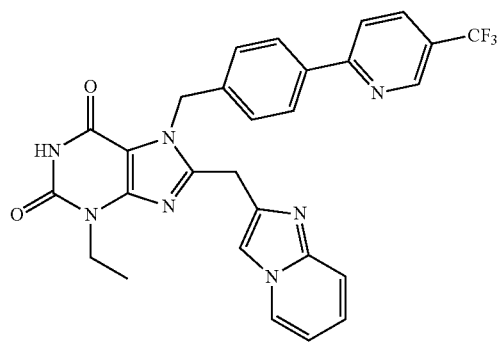
(I-12)
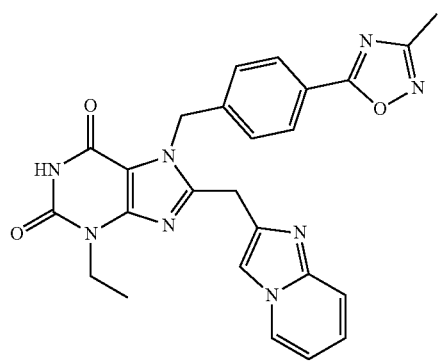
(I-13)
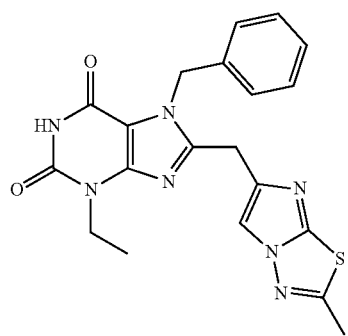
(I-14)
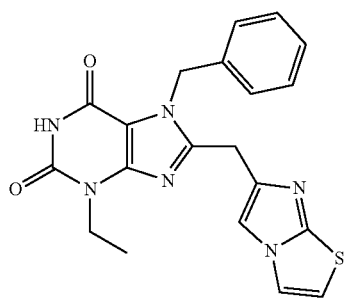
(I-15)
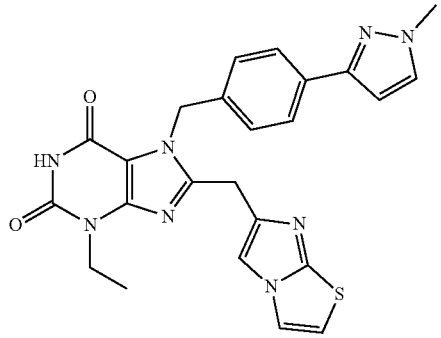
(I-16)
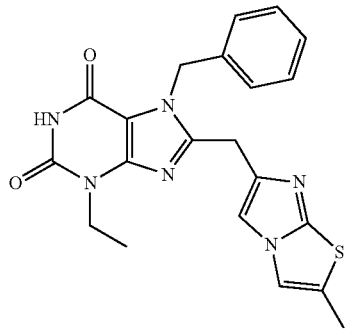
(I-17)
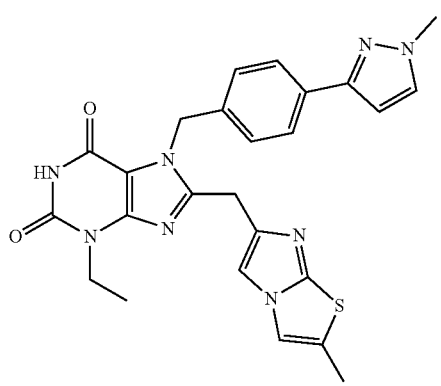

(I-18)
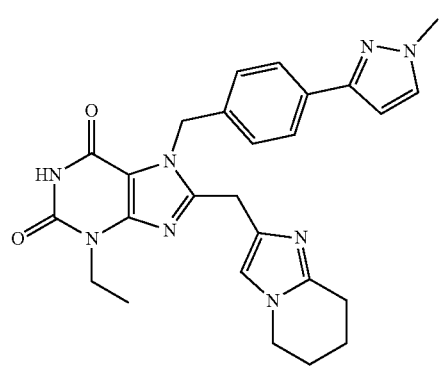
(I-19)
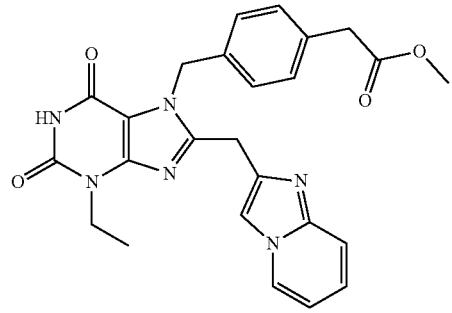
(I-20)
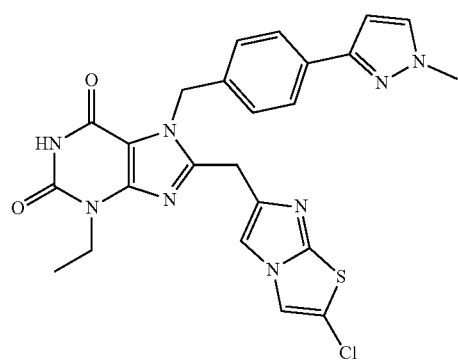
(I-21)
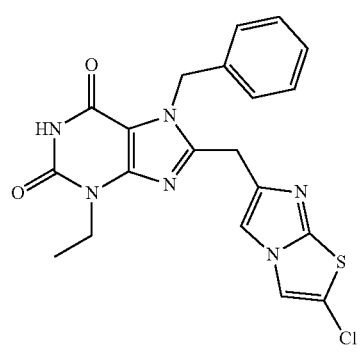
(I-22)
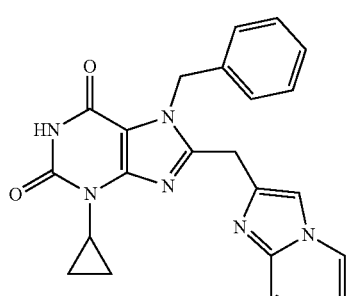
(I-23)
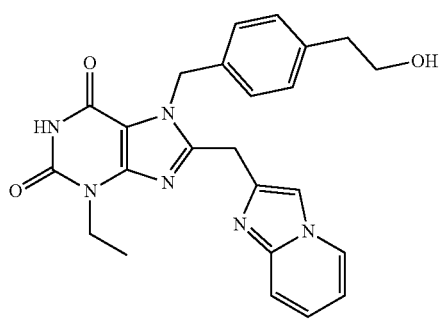
(I-24)
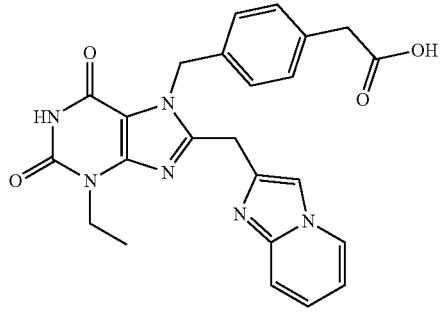
(I-25)
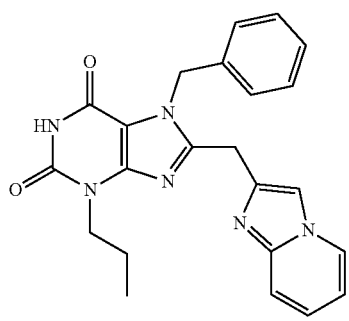
(I-26)
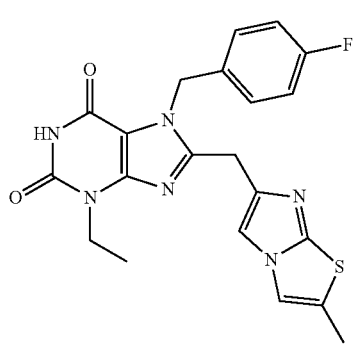

-continued
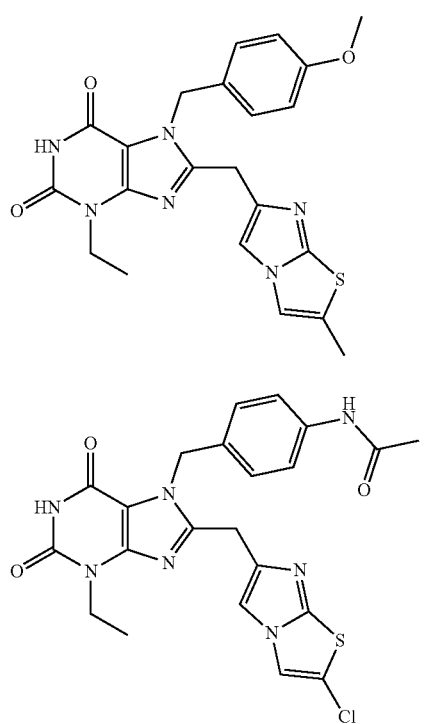
(I-27)
(I-28)
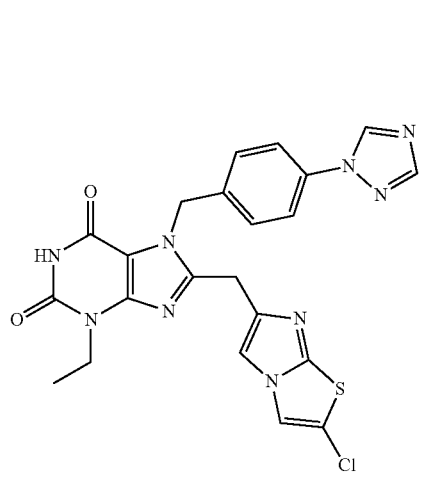
(I-29)
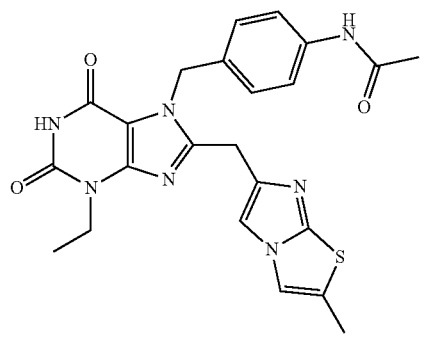
(I-30)
-continued
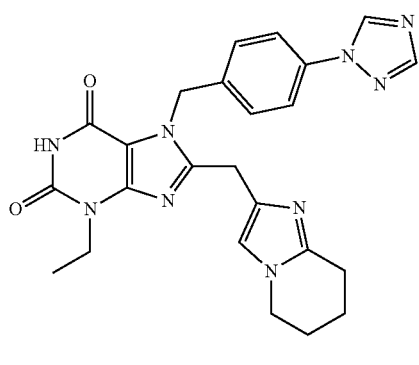
(I-31)
(I-32)
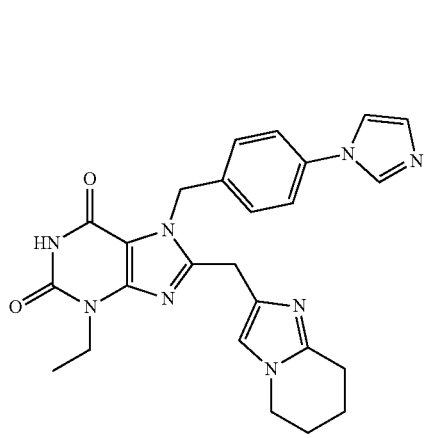
(I-33)
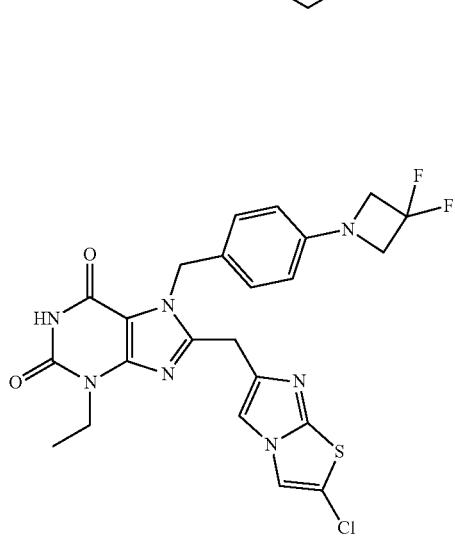
(I-34)

(I-35)
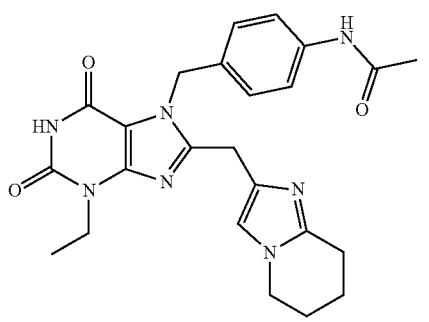

(I-36)
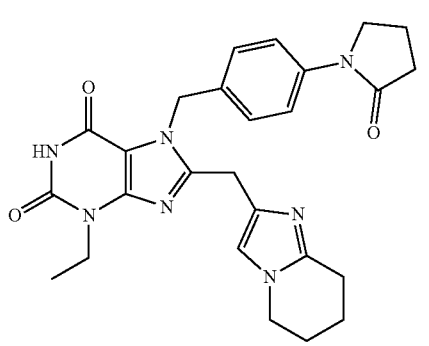

(I-37)
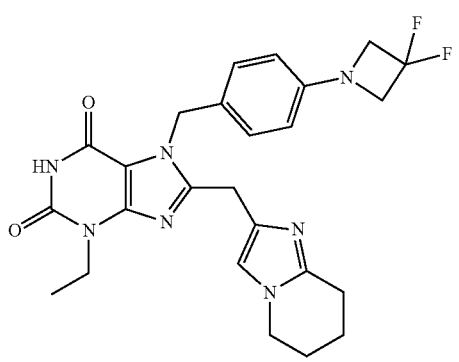

(I-38)
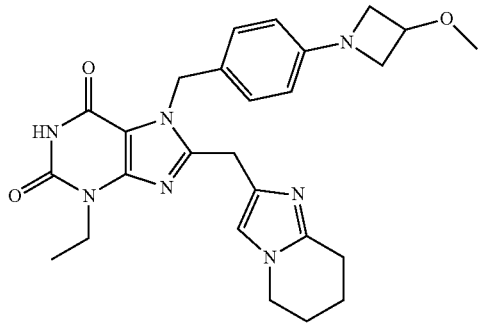

(I-39)
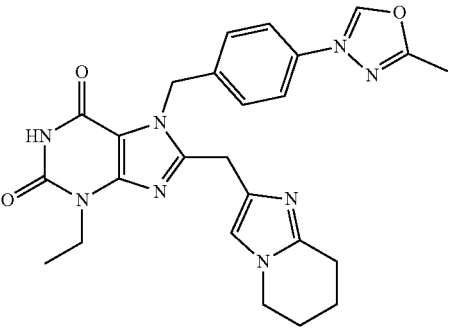

Preparation Process

Another subject of the present invention is a process for the preparation of the compounds of the formula I which is outlined below and by which the compounds of the formula I and intermediates in the course of their synthesis and salts thereof are obtainable. In general, the xanthine compounds of the formula I can be prepared, for example, in the course of a convergent synthesis, by linking two or more fragments which can be derived retrosynthetically from the formula I. More specifically, a suitably substituted xanthine derivative and a suitably substituted bicyclic compound can be employed as starting building blocks in the preparation of the compounds of formula I. The starting blocks can be synthesized from suitable precursor compounds, which allow the introduction of a variety of substituents into the various positions of the resulting xanthine derivative system and which can be chemically modified further in order to finally arrive at the compound of the formula I having the desired substituent pattern. In the synthesis of the xanthine derivatives, use can also be made of procedures and transformations which are described in the literature with respect to xanthine derivative preparation.

The starting materials employed in the synthesis of the compounds of the formula I are commercially available or can be prepared according to procedures, or in analogy to procedures, described in the literature or herein.

General Procedure:

In one synthetic approach for the preparation of compounds of the formula I, a compound of the formula II and a compound of the formula III are reacted to give a compound of the formula IV, which can already be the final compound of the formula I, or which is converted into the desired final compound of the formula I.

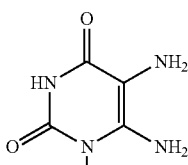

II

+

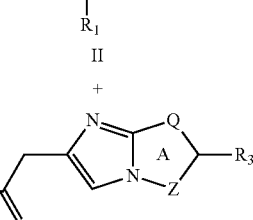

III

-continued

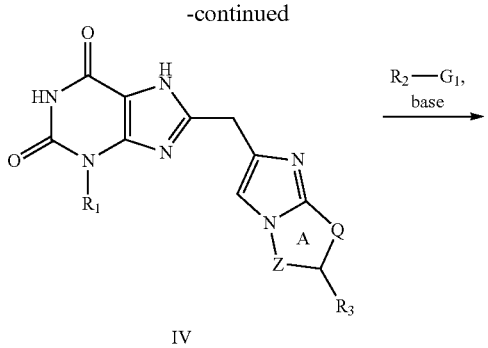

IV

More specifically, for the preparation of the compound of formula II, a compound of the formula V is obtained by reacting a cyanate with a primary amine to give a urea which is converted to the compound of the 6-aminouracil V followed by the oxidation with nitrite and reduction to give the compound of the formula II. The bicyclic compound of the formula III is obtained by reacting corresponding aromatic heterocycles with halogene-alkyl-3-oxobutonoates. The corresponding esters are saponified by reacting with NaOH to the compound of the formula III.

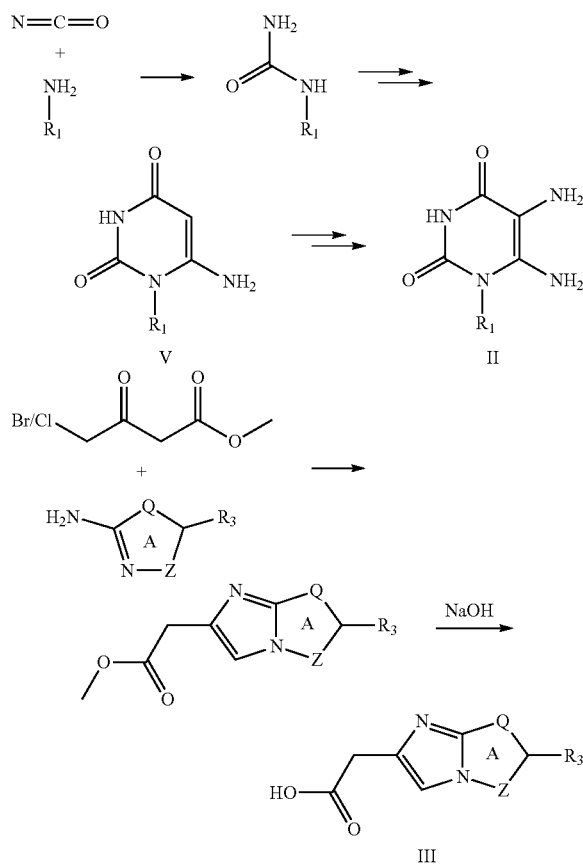

The groups $R_1$, $R_2$ and $R_3$, Z and Q in the compounds of the formulae II, III, IV, V, are defined as in the compounds of the formula I, and additionally functional groups may be present in protected form or in the form of a precursor group which is subsequently converted into the final group. The group $G_1$ attached to residue $R_2$ is a leaving group, such as a halogen, in particular bromine or chlorine, or a sulfonyloxy group, in particular trifluoromethanesulfonyloxy, methanesulfonyloxy, benzenesulfonyloxy or tosyloxy.

The starting compounds in the synthesis of the compounds of the formula I can also be employed, and the intermediates obtained and/or employed, in the form of salts, for example acid addition salts in case of basic compounds. The intermediates can also be present in another tautomeric form.

The reaction of the compounds of the formulae IV are, in general, extensively described in textbooks of peptide chemistry and synthesis.

The reaction of compounds of the formulae II with III to IV is generally carried out in an aprotic solvent such as a nitrile like acetonitrile, an ether like tetrahydrofuran or diglyme (di(2-methoxy-ethyl) ether), an amide like dimethylformamide, N-methylpyrrolidinone, dimethylacetamide, a sulfoxide like dimethylsulfoxide at temperatures from about 20° C. to about 200° C., for example at temperatures from about 30° C. to about 60° C. The reaction time generally is from about 30 minutes to about 48 hours, for example from about 5 hours to about 16 hours, depending on the particulars of the specific case and the chosen temperature range. Instead of using conventional heating, the reaction can also be carried out in a microwave oven utilizing microwave radiation at temperatures from about 60° C. to about 200° C., for example at temperatures from about 30° C. to about 60° C. In such case, the reaction time generally is from about 5 minutes to about 12 hours, for example from about 10 minutes to about 3 hours, depending on the particulars of the specific case and the chosen temperature range. A plethora of methods for the formation of the peptide bond have been reported. The most successful approaches known today involve active ester formation with uronium/guanidinium salts. The most popular members of this family are peptide synthesis reagents based on benzotriazole derivatives such as HOBt or HOAt, both of which are also commonly used as additives in carbodiimide mediated peptide coupling like (TBTU, HBTU, HATU, EDC, BtFFH, ByPOP) in situ with an organic or inorganic base such as an amine like triethylamine, ethyldiisopropylamine, N-methylmorpholine or 1,8-diazabicyclo[5.4.0]unde-7-ene is used for activation of the corresponding carboxylic acid.

The reaction of compounds of the formulae IV with $R_2$-$G_1$, a $S_N2$-type reaction, and is favourably carried out in the presence of a base, for example an alkali metal carbonate or alkali metal phosphate like cesium carbonate, sodium carbonate or tripotassium phosphate, in an inert solvent, such as a hydrocarbon like benzene, toluene or xylene, or an ether like tetrahydrofuran (THF), dioxane or 1,2-dimethoxyethane (DME), or an amide like dimethylformamide, N-methylpyrrolidinone, dimethylacetamide, a sulfoxide like dimethylsulfoxide, or a mixture of solvents, at temperatures from about 20° C. to about 200° C., for example at temperatures from about 30° C. to about 60° C. The reaction time generally is from about 30 minutes to about 48 hours, preferably from 30 minutes to about 16 hours, depending on particulars of the specific case and the chosen temperature range.

Nitro groups can be reduced to amino groups with various reducing agents, such as sulfides, dithionites, complex hydrides or by catalytic hydrogenation. A reduction of a nitro group may also be carried out at a later stage of the synthesis of a compound of the formula I, and a reduction of a nitro group to an amino group may also occur simultaneously with a reaction performed on another functional group, for example when reacting a group like a cyano group with hydrogen sulfide or when hydrogenating a group. In order to introduce these residues, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups can be hydrolyzed to the corresponding carboxylic acids under basic conditions in NaOH/MeOH and/or water, which after activation can then be reacted with amines or alcohols under standard conditions. Furthermore these esters can be hydrolyzed under acid conditions with HBr/AcOH.

The previously-mentioned reactions for the conversion of functional groups are furthermore, in general, extensively described in textbooks of organic chemistry in which details on the reactions and primary source literature can be found. Due to the fact that in the present case the functional groups are attached to xanthine derivatives it may in certain cases become necessary to specifically adapt reaction conditions or to choose specific reagents from a variety of reagents that can in principle be employed in a conversion reaction, or otherwise to take specific measures for achieving a desired conversion, for example to use protection group techniques. However, finding suitable reaction variants and reaction conditions in such cases does not cause any problems for one skilled in the art.

The structural elements present in the residues at the $R_1$, $R_2$ and $R_3$ position of the xanthine derivatives of the formula I can be introduced for example at the stage of a suitable precursor or the using the methods outlined above by consecutive reaction steps using parallel synthesis methodologies like those outlined below using procedures which per se are well known to one skilled in the art.

In the course of the preparation of the compounds of the formula I it can generally be advantageous or necessary to introduce functional groups which reduce or prevent undesired reactions or side reactions in the respective synthesis steps, in the form of precursor groups which are later converted into the desired functional groups, or to temporarily block functional groups by a protective group strategy suited to the synthesis problem. Such strategies are well known to those skilled in the art. Examples of precursor groups are cyano groups and nitro groups. The cyano group can, in a later step, be transformed into carboxylic acid derivatives or by reduction into aminomethyl groups. Nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art. For example, a phenolic hydroxy group can be attached to a trityl-polystyrene resin, which serves as a protecting group, and the molecule is cleaved from this resin by treatment with TFA or other acids at a later stage of the synthesis.

If a residue of the xanthine derivatives of the formula I are present in protected form or in the form of a precursor group, which have not already been introduced during a preceding step, for example during a synthesis of the xanthine derivative nucleus, these residues can, for example, be introduced the by standard alkylation procedures at 7-position of the nitrogen well-known to one skilled in the art. Alkylation of the aforementioned atom can, for example, be performed under standard conditions, preferably in the presence of a base like potassium carbonate, cesium carbonate, sodium hydride or potassium tert-butoxide, using an alkylating reagent containing a leaving group, like for example halogen like chlorine, bromine or iodine, or a sulfonyloxy group like tosyloxy, mesyloxy or trifluormethylsulfonyloxy. These standard procedures are known to the skilled person.

As is usual and applies to all reactions performed in the course of the synthesis of a compound of the formula I, appropriate details of the conditions applied in a specific preparation process, including the solvent, a base or acid, the temperature, the order of addition, the molar ratios and other parameters, are routinely chosen by the skilled person in view of the characteristics of the starting compounds and the target compound and the other particularities of the specific case. As is also known by the skilled person, not all processes described herein will in the same way be suitable for the preparation of all compounds of the formula I and their intermediates, and adaptations have to be made. In all processes for the preparation of the compounds of the formula I, workup of the reaction mixture and the purification of the product is performed according to customary methods known to the skilled person which include, for example, quenching of a reaction mixture with water, adjustment of a certain pH, precipitation, extraction, drying, concentration, crystallization, distillation and chromatography. As further examples of methods applicable in the synthesis of the compounds of the formula I, microwave assistance for speeding-up, facilitating or enabling reactions, may be mentioned, and modern separation techniques like preparative high pressure liquid chromatography (HPLC), which can be used for separating mixtures of positional isomers which may occur in any reactions. Also for the characterization of the product, customary methods are used such as NMR, IR and mass spectroscopy.

Another subject of the present invention are the novel starting compounds and intermediates occurring in the synthesis of the compounds of the formula I, including the compounds of the formulae II, III, IV, V wherein the groups $R^1$, $R^2$, $R^3$, Q, Z and $G_1$ in any of their stereoisomeric forms or a mixture of stereoisomeric forms in any ratio, and their salts, and their use as synthetic intermediates or starting compounds. All general explanations, specifications of embodiments and definitions of numbers and groups given above with respect to the compounds of the formula I apply correspondingly to the said intermediates and starting compounds. Subject of the invention are in particular the novel specific starting compounds and intermediates described herein. Independently thereof whether they are described as a free compound and/or as a specific salt, they are a subject of the invention both in the form of the free compounds and in the form of their salts, and if a specific salt is described, additionally in the form of this specific salt.

Pharmaceutical Preparations and Administration

When used in human or veterinary therapy, the xanthine compounds of Formula I and their pharmaceutically acceptable salts will generally be administered as a formulation in association with one or more pharmaceutically acceptable excipients. The term "excipient" is used herein to describe any ingredient other than the compound of the invention. The choice of excipient strongly depends on the particular mode of administration.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include: solid formulations such as tablets; capsules containing particulates, liquids, or powders; lozenges (including liquid-filled); and chews; multi- and nano-particulates; gels; solid solutions; liposomes; films, ovules, sprays and liquid formulations. Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

For tablet dosage forms, depending on dose, the drug may make up from 0.1 weight % to 80 weight % of the dosage form, more typically from 1 weight % to 60 weight % of the dosage form.

In addition to the drug, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also may contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Other possible ingredients include anti-oxidants, colourants, flavouring agents, flavour enhancers, preservatives, taste-masking agents, salivary stimulating agents, co-solvents (including oils), emollients, bulking agents and anti-foaming agents.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Other means of topical administration include delivery by electroporation, iontophoresis, phonophoresis, sonophoresis and microneedle or needle-free injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser, or nebuliser, with or without the use of a suitable propellant. For intranasal use, the powder may comprise a bioadhesive agent, for example, chitosan or cyclodextrin. The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Further modes of administration include rectal or vaginal administration, ocular or aural administration.

All formulations mentioned above may be formulated to be immediate and/or modified release. Modified release formulations include delayed-, sustained-, pulsed-, controlled-, targeted and programmed release.

According to the present invention, the xanthine derivative is administered preferably at an effective dose. An "effective dose" is the dose of the xanthine derivative that upon administration to a patient yields a measurable therapeutic effect with regard to the disease of interest. In the present invention an effective dose is the dose of the xanthine derivative that upon administration to a patient yields a therapeutic effect with regard to the level of serotonin in the corresponding organ.

For administration to human patients, the total daily dose of the compounds of the invention is typically in the range 0.001 mg to 5000 mg depending, of course, on the mode of administration. The total daily dose may be administered in single or divided doses and may, at the physician's discretion, fall outside of the typical range given herein.

As used herein, the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

DETAILED DESCRIPTION OF THE INVENTION

The invention will be described in more detail by way of preferred embodiments.

Definitions

Unless otherwise indicated, the term "alkyl" means a linear or branched and/or cyclic hydrocarbon, which is optionally substituted. Representative (C1-C10)-alkyl moieties include methyl, ethyl, n-propyl, isopropyl, n-butyl, isobutyl, t-butyl, n-pentyl, isopentyl, n-hexyl, isohexyl, n-heptyl, isoheptyl, n-octyl, isooctyl, n-nonyl, isononyl, and decyl. Cycloalkyl moieties include monocyclic alkyl groups or polycyclic alkyl groups bound or fused (annealed) together in a vicinal or geminal (spirocyclic bound) fashion. Representative cycloalkyl moieties include cyclopropyl, cyclobutyl, cyclopentyl, cyclohexyl, cycloheptyl and adamantyl. It is understood that in case of branched or cyclic alkyl groups the minimum chain length is C3.

Unless otherwise indicated, the term "alkenyl" means a linear, branched and/or cyclic hydrocarbon having at least one carbon-carbon double bond. Representative (C2-C10)-alkenyl moieties include vinyl (ethenyl), allyl (2-propenyl), 1-propenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative (C2-C10)-cycloalkenyl moieties include 1-cyclobutenyl, 2-cyclobutenyl, 2-cyclopentenyl, 3-cyclopentenyl, 2,4-cyclopentdienyl, 1-cyclohexyl, 2-cyclohexyl, 3-cyclohexyl, 2,5-cyclohexadienyl and cyclohepten. It is understood that in case of branched or cyclic alkenyl groups the minimum chain length is C4.

Unless otherwise indicated, the term "alkynyl" means a linear, branched and/or cyclic hydrocarbon having at least one carbon-carbon triple bond. Representative (C2-C10)-alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl. Representative (C2-C10)-cycloalkynyl moieties include cycloheptin, cyclooctin and cyclononin with arbitrary position of the triple bond. It is understood that in case of branched or cyclic alkynyl groups the minimum chain length is C4.

Unless otherwise indicated, the term "alkylene" means a bivalent alkyl moiety linking two other moieties.

Unless otherwise indicated, the term "alkenylene" means a bivalent alkenyl moiety linking two other moieties.

Unless otherwise indicated, the term "alkynylene" means a bivalent alkynyl moiety linking two other moieties.

Unless otherwise indicated, the term "aryl" means an aromatic ring or an aromatic or a partially aromatic ring system composed of carbon and hydrogen atoms. An aryl moiety may comprise multiple rings bound or fused together. Examples of aryl moieties include phenyl, biphenyl, anthracenyl, azulenyl, fluorenyl, indanyl, indenyl, naphthyl, phenanthrenyl, 1,2,3,4-tetrahydro-naphthalene and tolyl.

Unless otherwise indicated, the prefix "hetero" means that at least one carbon atom or carbon member in the hydrocarbon chain (e.g. —C— or —CH— or —CH$_2$—) is substituted by a hetero atom or hetero member, selected from oxygen (—O—), nitrogen (—N— or —N= or —NH—), sulfur (—S—), or phosphor (—P— or —PH— or). In aromatic or non-aromatic heterocycles, the prefix (Cn-Cm), with n and m being integers, defines the number of members of the heterocycle, irrespective whether the member is carbon or a hetero atom. For example, the term "(C5-C14)-heteroaryl" means a five- to fourteen-membered ring or ring system, in which at least one carbon atom or carbon member is substituted by a hetero atom or hetero member.

Unless otherwise indicated, the term "arylene" means a bivalent aryl moiety linking two other moieties.

Unless otherwise indicated, the term "heteroarylene" means a bivalent heteroaryl moiety linking two other moieties.

Unless otherwise indicated, the term "alkyl-arylene" or "alkyl-heteroarylene" means an alkyl moiety as defined above bound to a bivalent aryl moiety or to a bivalent heteroaryl moiety as defined above, respectively. Unless otherwise indicated, the term "alkenyl-arylene" or "alkenyl-heteroarylene" means an alkenyl moiety as defined above bound to a bivalent aryl moiety or to a bivalent heteroaryl moiety as defined above, respectively. Unless otherwise indicated, the term "alkynyl-arylene" or "alkynyl-heteroarylene" means an alkynyl moiety as defined above bound to a bivalent aryl moiety or to a bivalent heteroaryl moiety as defined above, respectively.

Unless otherwise indicated, the term "aryl-alkylene" or "heteroaryl-alkylene" means an aryl moiety or a heteroaryl moiety as defined above bound to an alkylene moiety as defined above, respectively. Likewise, the term "aryl-alkenylene" or "heteroaryl-alkenylene" means an aryl moiety or a heteroaryl moiety as defined above bound to an alkenylene moiety, respectively. Likewise, the term "aryl-alkynylene" or "heteroaryl-alkynylene" means an aryl moiety or a heteroaryl moiety as defined above bound to an alkynylene moiety, respectively.

Unless otherwise indicated, in composite systems such as "alkyl-arylene", "alkyl-heteroarylene", "alkenyl-arylene", "alkenyl-heteroarylene", "alkynyl-arylene", "alkynyl-heteroarylene", "aryl-alkylene", "heteroaryl-alkylene", "aryl-alkenylene", "heteroaryl-alkenylene", "aryl-alkynylene" and "heteroaryl-alkynylene" the prefix (Cn-Cm), with n and m being integers, defines the number of all members of the composite system. For instance, (C6-C15)-aryl-alkylene means that the system comprising the alkylene unit and the aryl unit is composed of six to fifteen members in total, except for further substituents if any.

Unless otherwise indicated, the phrase "bivalent group substituting a carbon moiety in the hydrocarbon chain of an alkyl, alkenyl, alkynyl, alkylene, alkenylene or alkynylene group" indicates the occurrence of a functional group in any position of the hydrocarbon chain. For instance, a (C1-C10)-alkyl group comprising the bivalent oxygen group —O— means a —(C0-$C_a$)-alkylene-O—(C0-$C_b$)-alkyl group, with (a+b)≤10. In this example, when the hetero oxygen atom is present at the C1-position, the group is an alkoxy group —O—($C_1$-$C_{10}$)-alkyl. When the hetero oxygen atom is present at an intermediate position, the group is an ether group.

For the purpose of the present invention and unless otherwise indicated, substituents generally comprise the following groups: fluoro —F, bromo —Br, chloro —Cl, hydroxyl —OH, (C1-C3)-alkyl, (C2-C3)-alkenyl, carbonyl —C(O)R, carboxyl —C(O)OH, carboxylate —C(O)O⁻, carboxy ester —$CO_2$R, alkoxy —OR, aldehyde —C(O)H, trihalide methyl ester —$OCX_3$, primary, secondary and tertiary amine —NR(R'), amide —N(R)—C(O)—R, imide —C(O)—N(R)—C(O)—R', carbamate —N(R)—C(O)—OR', carboxamide —C(O)N(R)(R'), carbimide —N(R)—C(O)—N(R')R", primary and secondary ketimine —(R)═NR', a secondary ketimine —(R)═NH, nitrile —CN, isonitrile, —NC, nitroxy —ONO, nitro —$NO_2$, nitrate —$ONO_2$, nitroso —NO, cyanate —OCN, isocyanate —NCO, sulfhydryl —SH, sulfide —SR, sulfurtrihalide —$SX_3$, sulfurpentahalide —$SX_5$, sulfinyl —S(O)R, sulfonyl —$SO_2$R, sulfino —$SO_2$H, sulfo —$SO_3$H, and combinations and salts thereof. In the aforementioned substituents R, R' and R" are hydrogen, (C1-C3)-alkyl or (C2-C3)-alkenyl, and X means a halide (F, Br, Cl). In some cases two or three identical or different substituents may be bound to one carbon atom. The term "combinations thereof" means that two or more of the aforementioned substituents may be linked together. For instance, a combination of a C1-alkyl group and a carboxy ester —$CO_2$R would be —$CH_2$—$CO_2$R.

EXAMPLES

When in the final step of the synthesis of a compound an acid such as trifluoroacetic acid or acetic acid was used, for example when trifluoroacetic acid was employed to an acid-labile protecting group (eg. a tert-butyl group) or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt, formic acid salt or trifluoroacetic acid salt or hydrochloric acid salt. Likewise starting materials or intermediates bearing a basic center like for example a basic nitrogen were either obtained and used as free base or in salt form like, for example, a trifluoroacetic acid salt, a hydrobromic acid salt, sulfuric acid salt, or a hydrochloric acid salt.

Abbreviations:
DCM Dichloromethane
dioxane [1,4]Dioxane
DMF N,N-Dimethylformamide
DMSO Dimethylsulfoxide
EtOAc Ethyl acetate
iPrOH Isopropanol
MeCN Acetonitrile
RT Room temperature (20° C. to 25° C.)
TFA Trifluoroacetic acid
LCMS Liquid Chromatography Mass Spectrometry
DIPEA N,N-Diisopropylethylamine
KOH Potassiumhydroxide
NaOH Sodium hydroxide
TBTU N,N,N',N'-Tetramethyl-O-(benzotriazol-1-yl)uronium tetrafluoroborate
HOBt Hydroxybenzotriazole
Hex Hexane
EtOH Ethanol LCMS (method 1): Instrument: Agilent Technologies 6230 Accurate Mass TOF LC/MS linked to Agilent Technologies HPLC 1260 Series; Column: Thermo Accuore RP-MS; Particle Size: 2.6 μM Dimension: 30×2.1 mm; Eluent A: $H_2O$ with 0.1% TFA Eluent B: MeCN with 0.1% TFA; Gradient: 0.00 min 95% A, 0.2 min 95% A, 1.1 min 1% A, 2.5 min Stoptime, 1.3 min Posttime; Flow rate: 0.8 ml/min; UV-detection: 220 nm, 254 nm, 300 nm.

LCMS (method 2): Gradient: 0.00 min 95% A, 0.2 min 95% A, 1.1 min 1% A, 3.0 min Stoptime, 1.3 min Posttime; Flow rate: 0.8 ml/min; UV-detection: 220 nm, 254 nm, 300 nm.

LCMS (method 3): Instrument: Agilent Technologies 6120 Quadrupole LC/MS linked to Agilent Technologies HPLC 1290 Infinity; Column: Thermo Accuore RP-MS; Particle Size: 2.6 μM Dimension: 30×2.1 mm; Eluent A: $H_2O$ with 0.1% TFA Eluent B: MeCN with 0.1% TFA; Gradient: 0.00 min 95% A, 0.2 min 95% A, 1.1 min 1% A, 2.5 min Stoptime, 1.3 min Posttime; Flow rate: 0.8 ml/min; UV-detection: 220 nm, 254 nm, 300 nm.

Examples 1-39

Xanthine derivatives according to general formula I were synthesized according to the following general procedure.

General Procedure

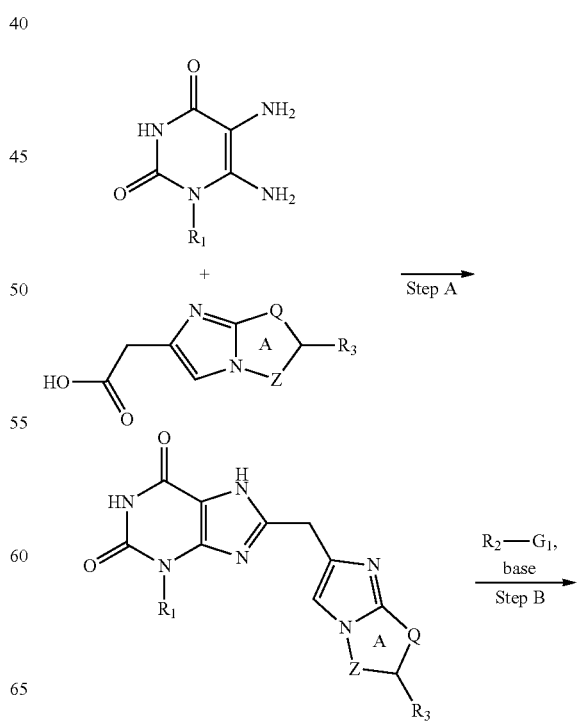

-continued

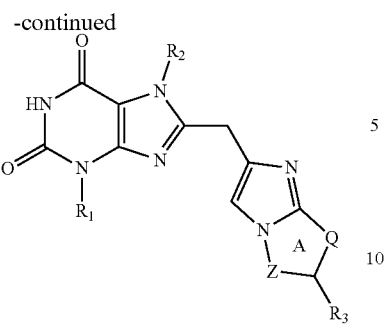

Synthesis of 2-(imidazo[1,2-a]pyridin-2-yl)acetic Acid

The title compound was prepared by adding 2-aminopyridine (20 g, 212 mmol) in 300 ml EtOH followed by 4-chloroacetoacetate (28.7 ml, 212 mmol) to a reaction vessel containing a magnetic stirring bar. The reaction mixture was stirred at 80° C. for 20 h. EtOH was evaporated and the crude mixture was solubilized in 100 ml 0.5 N HCl. The water phase was extracted three times with 50 ml DCM to remove organic impurities. The product remained in the aqueous phase which was removed under reduced pressure and give 37 g of the crude product. The crude product was purified by chromatography on silica gel eluting with a gradient of DCM/MeOH (Yield: 8.3 g 19%). The resulting ester was solubilized in 200 ml MeOH and 7 ml of 10 M NaOH solution was added. The reaction was stirred for 12 h at RT until the complete saponification of the ester. MeOH was evaporated and the aqueous phase was acidified to pH=7. The precipidated product was filtered off and washed with ether. (Yield: 7.6 g 99%). LCMS (method 1): $R_t$=0.435 min; HRMS (ESIpos): m/z [M+H]$^+$ calcd for $C_9H_8N_2O_2$ 177.0659. found, 177.0660.

Step A:

The acetic acid (10 mmol) and the 5,6-diamino-1-alkyl-1,2,3,4-tetrahydropyrimidine-2,4-dione (10 mmol) as starting materials were dissolved in 15 ml DMF. After addition of HOBt (15 mmol), TBTU (15 mmol) and DIPEA (60 mmol) the reaction was stirred for 20 h at RT. The solvent was removed under reduced pressure and solubilized in 215 ml of a 0.75 N NaOH solution. The mixture was stirred at 100° C. to dryness. The crude cyclised product was solubilized in 5 N HCl to pH=5 and washed three times with 50 ml EtOAc. The product remained in the aqueous phase which was removed under reduced pressure. The product was purified by chromatography on silica gel eluting with a gradient of DCM/MeOH. The fractions containing the product were combined and the solvent was evaporated under reduced pressure.

Step B:

The starting material (0.25 mmol) obtained in the previous step was dissolved in 15 ml DMF in a reaction vessel containing a magnetic stirring bar. 43.3 mg (0.5 mmol, 2 eq) NaHCO$_3$ were added followed by addition of alkylation reagent R$_2$-G$_1$ (0.26 mmol, 1.1 eq mmol), and the mixture was stirred for 16 h at RT. DMF was evaporated and the solid was homogenized in aqueous solution by means of sonification and was filtered off and dried under vacuum to give the crude product as intermediate. The crude product was purified by chromatography on silica gel eluting with a gradient of DCM/MeOH. The fractions containing the product were combined and the solvent was evaporated under reduced pressure.

Example 1: 8-((H-imidazo[1,2-a]pyridin-2-yl)methyl)-7-benzyl-3-ethyl-1H-purine-2,6(3H,7H)-dione (KM-06-30)

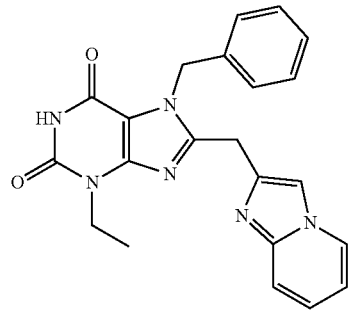

(I-1)

Synthesis of 3-ethyl-8-(imidazo[1,2-a]pyridin-2-ylmethyl)-3,7-dihydro-1H-purine-2,6-dione According to step A the title compound was prepared by adding 2 g (11.8 mmol) 5,6-diamino-1-ethyl-1,2,3,4-tetrahydropyrimidine-2,4-dione in 100 ml DMF, 2.1 g (12 mmol) 2-(imidazo[1,2-a]pyridin-2-yl)acetic acid, HOBt (2.7 g, 17.7 mmol) and a peptide coupling reagent like TBTU (5.7 g, 17.7 mmol) to a reaction vessel containing a magnetic stirring bar, followed by 12.4 ml DIPEA (71 mmol). The reaction mixture was stirred at RT for 20 h. DMF was evaporated and the crude N-(6-amino-1-ethyl-1,2,3,4-tetrahydro-2,4-dioxopyrimidin-5-yl)-2-(H-imidazo[1,2-a]pyridin-2-yl)acetamide was dissolved in 215 ml of a 0.75 N NaOH solution. The reaction mixture was heated to 100° C. to dryness. The crude cyclised product was solubilized in 0.5 N HCl to pH=5. The aqueous phase was extracted three times with 50 ml EtOAc. The product remained in the aqueous phase which was removed under reduced pressure. The product was purified by chromatography on silica gel eluting with a gradient of DCM/MeOH. The fractions containing the product were combined and the solvent was evaporated under reduced pressure (Yield 970 mg, 26%).

$^1$H NMR (300 MHz, DMSO-d6) δ 10.91 (s, 1H), 8.48 (d, J=6.9 Hz, 1H), 7.75 (s, 1H), 7.46 (d, J=9.1 Hz, 1H), 7.24-7.13 (m, 1H), 6.89-6.78 (m, 1H), 4.16 (s, 2H), 3.93 (q, J=7.2 Hz, 2H), 1.18 (t, J=7.1 Hz, 3H). LCMS (method 1): $R_t$=0.201 min; HRMS (ESIpos): m/z [M+H]$^+$ calcd for $C_{15}H_{14}N_6O_2$ 311.1251. found, 311.1265.

Synthesis of 8-((H-imidazo[1,2-a]pyridin-2-yl)methyl)-7-benzyl-3-ethyl-1H-purine-2,6(3H,7H)-dione According to step B 80 mg (0.26 mmol) 3-ethyl-8-(imidazo[1,2-a]pyridin-2-ylmethyl)-3,7-dihydro-1H-purine-2,6-dione was dissolved in 15 ml DMF in a reaction vessel containing a magnetic stirring bar. 43.3 mg (0.5 mmol, 2 eq) NaHCO$_3$ were added followed by sequential addition of 46 μl Benzylbromide (0.39 mmol, 1.5 eq mmol). The mixture was stirred for 16 h at RT. DMF was evaporated and the solid was homogenized in aqueous solution by means of sonification and was filtered off and dried under vacuum to give the crude product as intermediate. The crude product was purified by chromatography on silica gel eluting with a gradient of DCM/MeOH. The fractions containing the product were combined and the solvent was evaporated under reduced pressure (Yield: 46 mg, 51%).

$^1$H NMR (300 MHz, DMSO-d$_6$) δ 11.14 (s, 1H), 8.40 (d, J=6.7 Hz, 1H), 7.70 (s, 1H), 7.45 (d, J=9.1 Hz, 1H), 7.28-7.12 (m, 6H), 6.83 (t, J=6.7 Hz, 1H), 5.61 (s, 2H), 4.22 (s, 2H), 3.95 (q, J=7.1 Hz, 2H), 1.20 (t, J=7.1 Hz, 3H). LCMS (method 1): R$_t$=0.976 min; HRMS (ESIpos): m/z [M+H]$^+$ calcd for C$_{22}$H$_{20}$N$_6$O$_2$ 401.1726. found, 401.1726.

Example 2: 7-benzyl-3-ethyl-8-((5,6,7,8-tetrahydro-imidazo[1,2-a]pyridin-2-yl)methyl)-3,7-dihydro-1H-purine-2,6-dione (KM-06-57)

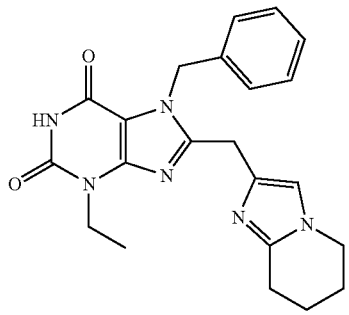

(I-2)

$^1$H NMR (300 MHz, DMSO-d$_6$) δ 11.10 (s, 1H), 7.32-7.24 (m, 3H), 7.10 (d, J=6.8 Hz, 2H), 6.69 (s, 1H), 5.59 (s, 2H), 3.94 (q, J=7.1 Hz, 2H), 3.89 (s, 2H), 3.75 (t, J=5.7 Hz, 2H), 2.59 (t, J=6.1 Hz, 2H), 1.84-1.70 (m, 4H), 1.20 (t, J=7.1 Hz, 3H). LCMS (method 1): R$_t$=1.017 min; HRMS (ESIpos): m/z [M+H]$^+$ calcd for C$_{22}$H$_{24}$N$_6$O$_2$ 405.2034. found, 405.2036.

Example 3: 7-([1,1'-biphenyl]-4-ylmethyl)-3-ethyl-8-((5,6,7,8-tetrahydroimidazo[1,2-a]pyridin-2-yl)methyl)-3,7-dihydro-1H-purine-2,6-dione (KM-06-70)

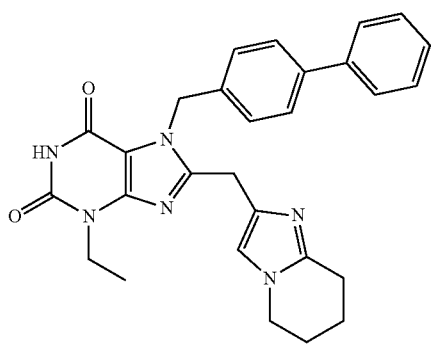

(I-3)

$^1$H NMR (300 MHz, DMSO-d$_6$) δ 11.10 (s, 1H), 7.61 (dd, J=7.8, 10.9 Hz, 4H), 7.45 (t, J=7.6 Hz, 2H), 7.35 (t, J=7.3 Hz, 1H), 7.17 (d, J=8.2 Hz, 2H), 6.71 (s, 1H), 5.63 (s, 2H), 3.95 (d, J=9.2 Hz, 4H), 3.73 (t, J=5.7 Hz, 2H), 2.58 (t, J=6.0 Hz, 2H), 1.72 (q, J=6.7 Hz, 4H), 1.21 (t, J=7.0 Hz, 5H). LCMS (method 1): R$_t$=1.162 min; HRMS (ESIpos): m/z [M+H]$^+$ calcd for C$_{28}$H$_{28}$N$_6$O$_2$ 481.2347. found, 481.2333.

Example 4: Methyl 4-((8-((H-imidazo[1,2-a]pyridin-2-yl)methyl)-3-ethyl-1,2,3,6-tetrahydro-2,6-dioxopurin-7-yl)methyl)benzoate (KM-06-78)

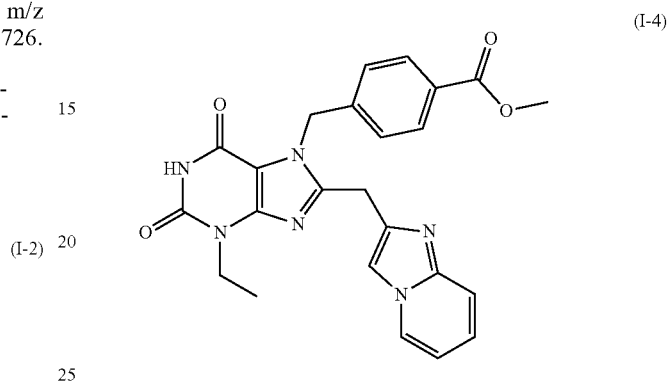

(I-4)

$^1$H NMR (300 MHz, DMSO-d$_6$) δ 11.14 (s, 1H), 8.31 (d, J=6.7 Hz, 1H), 7.71 (d, J=8.3 Hz, 2H), 7.61 (s, 1H), 7.36 (d, J=9.1 Hz, 1H), 7.17-7.08 (m, 3H), 6.80-6.73 (m, 1H), 5.66 (s, 2H), 4.24 (s, 2H), 3.97 (q, J=7.0 Hz, 2H), 3.80 (s, 3H), 1.23 (t, J=7.1 Hz, 3H). LCMS (method 1): R$_t$=0.951 min; HRMS (ESIpos): m/z [M+H]$^+$ calcd for C$_{24}$H$_{22}$N$_6$O$_4$ 459.1775. found, 459.1785.

Example 5: 8-((H-imidazo[1,2-a]pyridin-2-yl)methyl)-7-((benzo[d][1,3]dioxol-5-yl)methyl)-3-ethyl-1H-purine-2,6(3H,7H)-dione (KM-06-79)

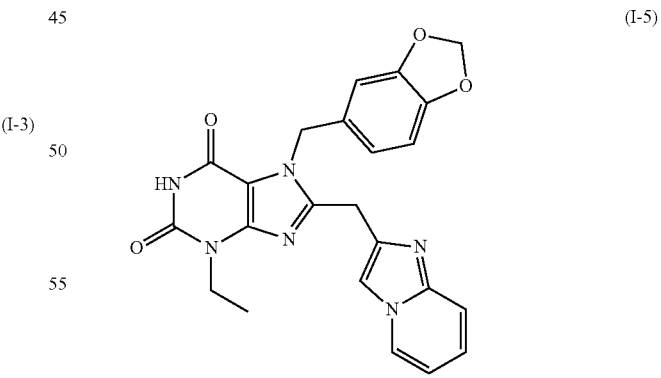

(I-5)

$^1$H NMR (300 MHz, DMSO-d$_6$) δ 11.14 (s, 1H), 8.42 (d, J=6.8 Hz, 1H), 7.69 (s, 1H), 7.45 (d, J=9.1 Hz, 1H), 7.23-7.14 (m, 1H), 6.87-6.80 (m, 1H), 6.79-6.71 (m, 2H), 6.65 (d, J=8.1 Hz, 1H), 5.92 (s, 2H), 5.48 (s, 2H), 4.25 (s, 2H), 3.94 (q, J=7.0 Hz, 2H), 1.20 (t, J=7.0 Hz, 3H). LCMS (method 1): R$_t$=0.968 min; HRMS (ESIpos): m/z [M+H]$^+$ calcd for C$_{23}$H$_{20}$N$_6$O$_4$ 445.1619. found, 445.1621.

Example 6: 4-((3-ethyl-8-(imidazo[1,2-a]pyridin-2-ylmethyl)-2,6-dioxo-1,2,3,6-tetrahydro-7H-purin-7-yl)methyl)benzoic Acid (KM-06-80)

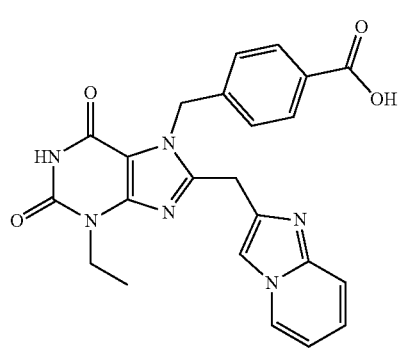
(I-6)

$^1$H NMR (300 MHz, DMSO-d$_6$) δ 11.13 (s, 1H), 8.36 (d, J=6.7 Hz, 1H), 7.74 (d, J=8.1 Hz, 2H), 7.68 (s, 1H), 7.39 (d, J=9.1 Hz, 1H), 7.14 (d, J=8.2 Hz, 3H), 6.83-6.74 (m, 1H), 5.66 (s, 2H), 4.24 (s, 2H), 3.96 (q, J=6.7 Hz, 2H), 1.22 (t, J=6.9 Hz, 3H). LCMS (method 1): R$_t$=0.565 min; HRMS (ESIpos): m/z [M+H]$^+$ calcd for C$_{23}$H$_{20}$N$_6$O$_4$ 445.1619. found, 445.1620.

Example 7: 3-ethyl-8-(imidazo[1,2-a]pyridin-2-ylmethyl)-7-(4-(1-methyl-1H-pyrazol-3-yl)benzyl)-3,7-dihydro-1H-purine-2,6-dione (KM-06-81)

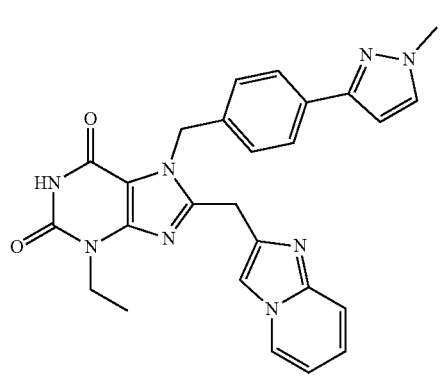
(I-7)

$^1$H NMR (300 MHz, DMSO-d$_6$) δ 11.14 (s, 1H), 8.41 (d, J=6.7 Hz, 1H), 7.74 (s, 1H), 7.70 (d, J=2.4 Hz, 1H), 7.66 (d, J=8.3 Hz, 2H), 7.46 (d, J=9.1 Hz, 1H), 7.22-7.13 (m, 3H), 6.85-6.78 (m, 1H), 6.60 (d, J=2.4 Hz, 1H), 5.62 (s, 2H), 4.24 (s, 2H), 3.95 (q, J=7.1 Hz, 2H), 3.86 (s, 3H), 1.20 (t, J=7.1 Hz, 3H). LCMS (method 1): R$_t$=1.030 min; HRMS (ESIpos): m/z [M+H]$^+$ calcd for C$_{26}$H$_{24}$N$_6$O$_2$ 481.2095. found, 481.2090.

Example 8: 7-(4-(5-methyl-1,2,4-oxadiazol-3-yl)benzyl)-8-((H-imidazo[1,2-a]pyridin-2-yl)methyl)-3-ethyl-1H-purine-2,6(3H,7H)-dione (KM-06-82)

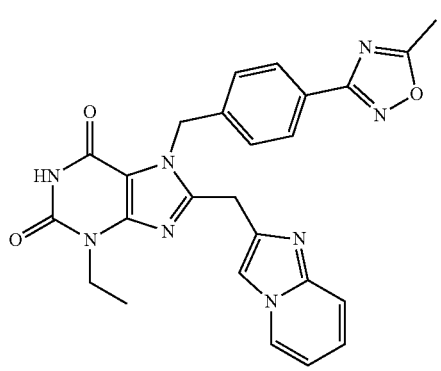
(I-8)

$^1$H NMR (300 MHz, DMSO-d$_6$) δ 11.14 (s, 1H), 8.34 (d, J=6.7 Hz, 1H), 7.79 (d, J=8.2 Hz, 2H), 7.67 (s, 1H), 7.38 (d, J=9.0 Hz, 1H), 7.21 (d, J=8.4 Hz, 2H), 7.14-7.07 (m, 1H), 6.77-6.70 (m, 1H), 5.67 (s, 2H), 4.26 (s, 2H), 3.97 (q, J=7.1 Hz, 2H), 2.65 (s, 3H), 1.22 (t, J=7.0 Hz, 3H). LCMS (method 1): R$_t$=1.056 min; HRMS (ESIpos): m/z [M+H]$^+$ calcd for C$_{25}$H$_{22}$N$_8$O$_3$ 483.1888. found, 483.1875.

Example 9: 3-ethyl-8-(imidazo[1,2-a]pyridin-2-ylmethyl)-7-(4-(pyrimidin-2-yl)benzyl)-3,7-dihydro-1H-purine-2,6-dione (KM-06-89)

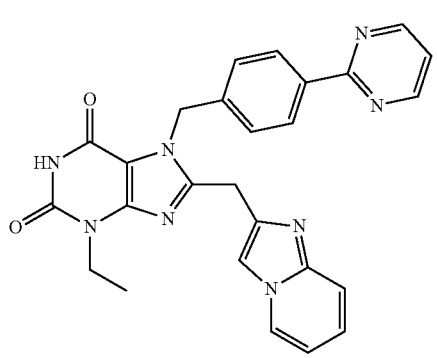
(I-9)

$^1$H NMR (300 MHz, DMSO-d$_6$) δ 11.15 (s, 1H), 8.87 (d, J=5.0 Hz, 2H), 8.35 (d, J=6.9 Hz, 1H), 8.23 (d, J=8.2 Hz, 2H), 7.70 (s, 1H), 7.41 (d, J=6.0 Hz, 1H), 7.24 (d, J=8.2 Hz, 2H), 7.14-7.05 (m, 1H), 6.76-6.68 (m, 1H), 5.69 (s, 2H), 4.26 (s, 2H), 3.97 (q, J=7.2 Hz, 2H), 1.22 (t, J=7.1 Hz, 3H). LCMS (method 1): R$_t$=0.995 min; HRMS (ESIpos): m/z [M+H]$^+$ calcd for C$_{26}$H$_{22}$N$_8$O$_2$ 479.1938. found, 479.1948.

Example 10: 3-ethyl-8-(imidazo[1,2-a]pyridin-2-ylmethyl)-7-(4-(thiazol-2-yl)benzyl)-3,7-dihydro-1H-purine-2,6-dione (KM-06-90)

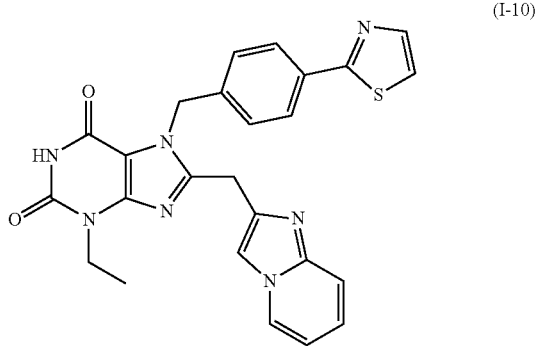 [SMILES: CCn1c(=O)[nH]c(=O)c2c1nc(Cc1cn3ccccc3n1)n2Cc1ccc(-c2nccs2)cc1]
(I-10)

¹H NMR (300 MHz, DMSO-d₆) δ 11.16 (s, 1H), 8.35 (d, J=6.7 Hz, 1H), 7.89 (d, J=3.3 Hz, 1H), 7.79-7.71 (m, 3H), 7.68 (s, 1H), 7.40 (d, J=9.1 Hz, 1H), 7.18 (d, J=8.3 Hz, 2H), 7.14-7.06 (m, 1H), 6.76-6.69 (m, 1H), 5.65 (s, 2H), 4.27 (s, 2H), 3.97 (q, J=7.1 Hz, 2H), 1.22 (t, J=7.0 Hz, 3H). LCMS (method 1): $R_t$=1.036 min; HRMS (ESIpos): m/z [M+H]⁺ calcd for $C_{26}H_{21}N_7O_2S$ 484.1550. found, 484.1561.

Example 11: 3-ethyl-8-(imidazo[1,2-a]pyridin-2-ylmethyl)-7-(4-(5-(trifluoromethyl)pyridin-2-yl)benzyl)-3,7-dihydro-1H-purine-2,6-dione (KM-06-91)

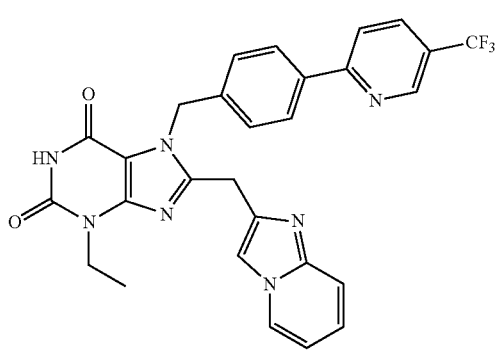
(I-11)

¹H NMR (300 MHz, DMSO-d₆) δ 11.16 (s, 1H), 9.04-8.99 (m, 1H), 8.35 (d, J=6.7 Hz, 1H), 8.26 (dd, J=8.5, 2.7 Hz, 1H), 8.06 (d, J=8.5 Hz, 1H), 7.98 (d, J=8.4 Hz, 2H), 7.69 (s, 1H), 7.41 (d, J=9.1 Hz, 1H), 7.24 (d, J=8.4 Hz, 2H), 7.14-7.06 (m, 1H), 6.77-6.69 (m, 1H), 5.68 (s, 2H), 4.28 (s, 2H), 3.96 (q, J=7.0 Hz, 2H), 1.22 (t, J=7.0 Hz, 3H). LCMS (method 1): $R_t$=1.166 min; HRMS (ESIpos): m/z [M+H]⁺ calcd for $C_{26}H_{22}F_3N_7O_2$ 546.1860. found, 546.1867.

Example 12: 3-ethyl-8-(imidazo[1,2-a]pyridin-2-ylmethyl)-7-(4-(3-methyl-1,2,4-oxadiazol-5-yl)benzyl)-3,7-dihydro-1H-purine-2,6-dione (KM-06-93)

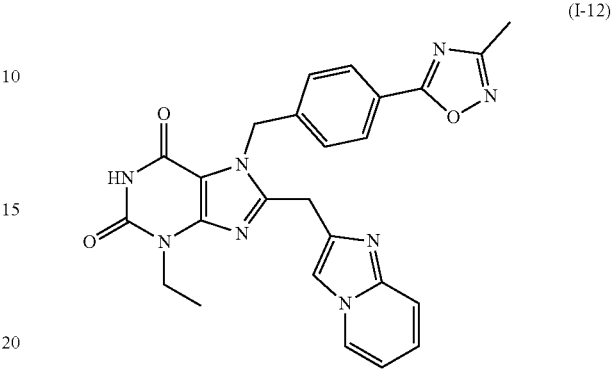
(I-12)

¹H NMR (300 MHz, DMSO-d₆) δ 11.15 (s, 1H), 8.28 (d, J=6.9 Hz, 1H), 7.81 (d, J=8.2 Hz, 2H), 7.61 (s, 1H), 7.33 (d, J=9.1 Hz, 1H), 7.19 (d, J=8.2 Hz, 2H), 7.09-7.00 (m, 1H), 6.72-6.63 (m, 1H), 5.68 (s, 2H), 4.28 (s, 2H), 3.98 (q, J=7.1 Hz, 2H), 2.40 (s, 3H), 1.24 (t, J=7.1 Hz, 3H). LCMS (method 1): $R_t$=1.039 min; HRMS (ESIpos): m/z [M+H]⁺ calcd for $C_{25}H_{22}N_8O_3$ 483.1888. found, 483.1888.

Example 13: 7-benzyl-3-ethyl-8-((2-methylimidazo[2,1-b][1,3,4]thiadiazol-6-yl)methyl)-3,7-dihydro-1H-purine-2,6-dione (KM-06-66)

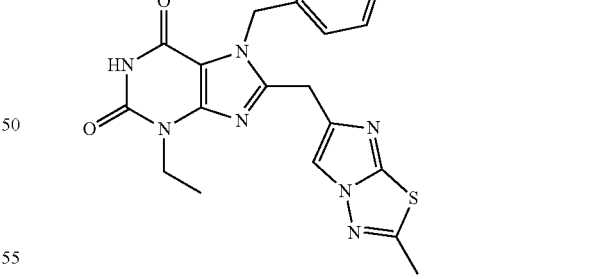
(I-13)

¹H NMR (300 MHz, DMSO-d₆) δ 11.11 (s, 1H), 7.82 (s, 1H), 7.29-7.19 (m, 3H), 7.10 (d, J=7.1 Hz, 2H), 5.59 (s, 2H), 4.11 (s, 2H), 3.94 (q, J=7.1 Hz, 2H), 2.66 (s, 3H), 1.20 (t, J=6.9 Hz, 3H). LCMS (method 1): $R_t$=1.159 min; HRMS (ESIpos): m/z [M+H]⁺ calcd for $C_{20}H_{19}N_7O_2S$ 422.1394. found, 422.1387.

Example 14: 7-benzyl-3-ethyl-8-(imidazo[2,1-b]thiazol-6-ylmethyl)-3,7-dihydro-1H-purine-2,6-dione (KM-06-64)

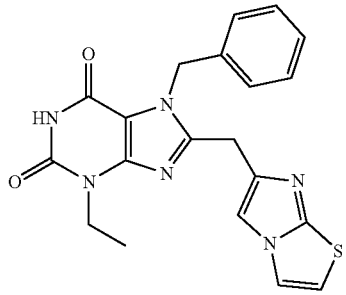

(I-14)

$^1$H NMR (300 MHz, DMSO-d$_6$) δ 11.12 (s, 1H), 7.77 (d, J=4.5 Hz, 1H), 7.55 (s, 1H), 7.30-7.20 (m, 3H), 7.19-7.15 (m, 1H), 7.15-7.09 (m, 2H), 5.61 (s, 2H), 4.11 (s, 2H), 3.94 (q, J=7.2 Hz, 2H), 1.20 (t, J=7.1 Hz, 3H). LCMS (method 1): R$_t$=1.093 min; HRMS (ESIpos): m/z [M+H]$^+$ calcd for C$_{20}$H$_{18}$N$_6$O$_2$S 407.1285. found, 407.1285.

Example 15: 7-(4-(1-methyl-1H-pyrazol-3-yl)benzyl)-3-ethyl-8-((imidazo[2,1-b]thiazol-6-yl)methyl)-1H-purine-2,6(3H,7H)-dione (KM-06-96)

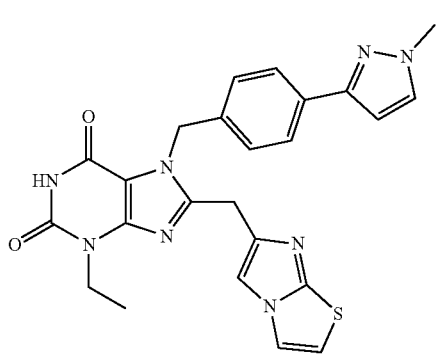

(I-15)

$^1$H NMR (300 MHz, DMSO-d$_6$) δ 11.13 (s, 1H), 7.78 (d, J=4.6 Hz, 1H), 7.73-7.63 (m, 3H), 7.60 (s, 1H), 7.22-7.11 (m, 3H), 6.61 (s, 1H), 5.62 (s, 2H), 4.13 (s, 2H), 3.95 (q, J=7.1 Hz, 2H), 3.86 (s, 3H), 1.20 (t, J=7.1 Hz, 3H). LCMS (method 1): R$_t$=1.162 min; HRMS (ESIpos): m/z [M+H]$^+$ calcd for C$_{24}$H$_{22}$N$_8$O$_2$S 487.1659. found, 487.1657.

Example 16: 7-benzyl-3-ethyl-8-((2-methylimidazo[2,1-b]thiazol-6-yl)methyl)-1H-purine-2,6(3H,7H)-dione (KM-06-97)

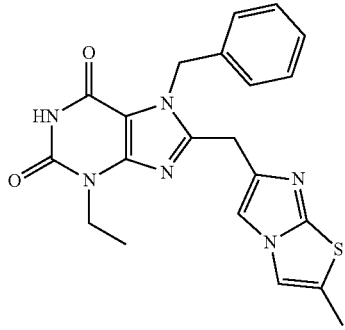

(I-16)

$^1$H NMR (300 MHz, DMSO-d$_6$) δ 11.12 (s, 1H), 7.53 (s, 1H), 7.45 (s, 1H), 7.31-7.20 (m, 3H), 7.13 (d, J=6.7 Hz, 2H), 5.60 (s, 2H), 4.07 (s, 2H), 3.94 (q, J=7.1 Hz, 2H), 2.35 (s, 3H), 1.20 (t, J=7.0 Hz, 3H). LCMS (method 1): R$_t$=1.195 min; HRMS (ESIpos): m/z [M+H]$^+$ calcd for C$_{21}$H$_{10}$N$_6$O$_2$S 421.1441. found, 421.1450.

Example 17: 3-ethyl-7-(4-(1-methyl-1H-pyrazol-3-yl)benzyl)-8-((2-methylimidazo[2,1-b]thiazol-6-yl)methyl)-3,7-dihydro-1H-purine-2,6-dione (KM-06-98)

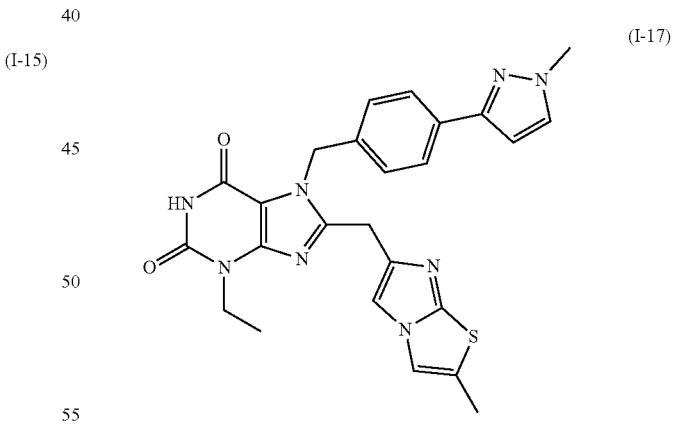

(I-17)

$^1$H NMR (300 MHz, DMSO-d$_6$) δ 11.13 (s, 1H), 7.70 (d, J=2.4 Hz, 1H), 7.63 (d, J=8.2 Hz, 2H), 7.47 (s, 1H), 7.43 (s, 1H), 7.10 (d, J=8.3 Hz, 2H), 6.60 (d, J=2.4 Hz, 1H), 5.59 (s, 2H), 4.10 (s, 2H), 3.95 (q, J=7.1 Hz, 2H), 2.26 (s, 3H), 1.21 (t, J=7.1 Hz, 3H). LCMS (method 1): R$_t$=1.179 min; HRMS (ESIpos): m/z [M+H]$^+$ calcd for C$_{25}$H$_{24}$N$_8$O$_2$S 501.1816. found, 501.1825.

Example 18: 7-(4-(1-methyl-1H-pyrazol-3-yl)benzyl)-3-ethyl-8-((5,6,7,8-tetrahydroimidazo[1,2-a]pyridin-2-yl)methyl)-1H-purine-2,6(3H,7H)-dione (KM-06-099)

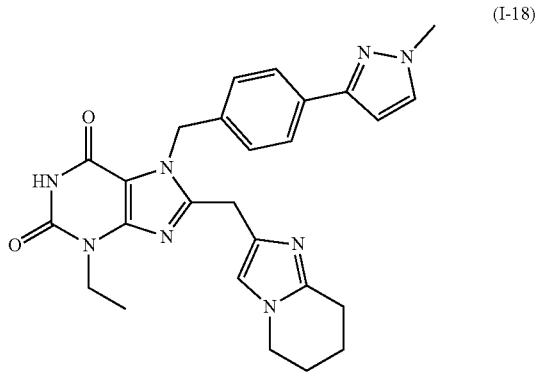 [SMILES: CCn1c(=O)[nH]c(=O)c2c1nc(Cc1cn3c(n1)CCCC3)n2Cc1ccc(-c2ccn(C)n2)cc1]

(I-18)

$^1$H NMR (300 MHz, DMSO-d$_6$) δ 11.12 (s, 1H), 7.71 (d, J=2.4 Hz, 1H), 7.68 (d, J=8.2 Hz, 2H), 7.10 (d, J=8.3 Hz, 2H), 6.68 (s, 1H), 6.63 (d, J=2.4 Hz, 1H), 5.59 (s, 2H), 3.99-3.89 (m, 4H), 3.86 (s, 3H), 3.72 (t, J=5.6 Hz, 2H), 2.59 (t, J=6.0 Hz, 2H), 1.80-1.66 (m, 4H), 1.21 (t, J=6.7 Hz, 3H). LCMS (method 1): R$_t$=1.012 min; HRMS (ESIpos): m/z [M+H]$^+$ calcd for C$_{26}$H$_{28}$N$_8$O$_2$ 485.2408. found, 485.2413.

Example 19: methyl 2-(4-((3-ethyl-8-(imidazo[1,2-a]pyridin-2-ylmethyl)-2,6-dioxo-1,2,3,6-tetrahydro-7H-purin-7-yl)methyl)phenyl)acetate (KM-06-106)

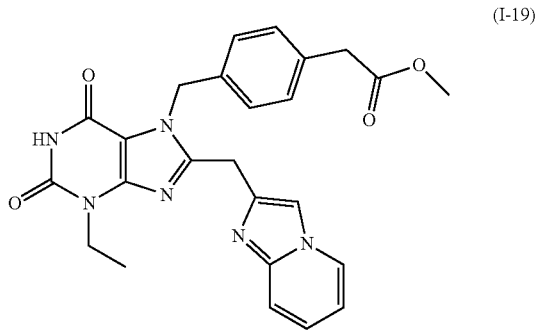 [SMILES: CCn1c(=O)[nH]c(=O)c2c1nc(Cc1cn3ccccc3n1)n2Cc1ccc(CC(=O)OC)cc1]

(I-19)

$^1$H NMR (300 MHz, DMSO-d$_6$) δ 11.11 (s, 1H), 8.41 (d, J=6.7 Hz, 1H), 7.70 (s, 1H), 7.46 (d, J=9.2 Hz, 1H), 7.20 (ddd, J=9.2, 6.7, 1.4 Hz, 1H), 7.15 (d, J=8.4 Hz, 2H), 7.12 (d, J=8.2 Hz, 2H), 6.86-6.83 (m, 1H), 5.60 (s, 2H), 4.24 (s, 2H), 3.96 (q, J=7.1 Hz, 2H), 3.60 (s, 3H), 3.60 (s, 2H), 1.22 (t, J=7.1 Hz, 3H). LCMS (method 2): R$_t$=1.142 min; HRMS (ESIpos): m/z [M+H]$^+$ calcd for C$_{25}$H$_{24}$N$_6$O$_4$ 473.1932. found, 473.1937.

Example 20: 8-((2-chloroimidazo[2,1-b]thiazol-6-yl)methyl)-3-ethyl-7-(4-(1-methyl-1H-pyrazol-3-yl)benzyl)-3,7-dihydro-1H-purine-2,6-dione (KM-06-107)

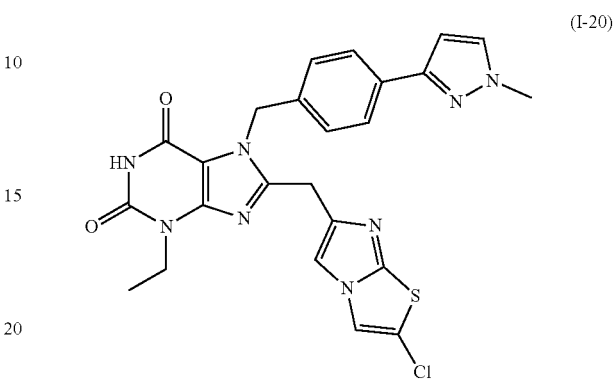

(I-20)

$^1$H NMR (300 MHz, DMSO-d$_6$) δ 11.12 (s, 1H), 8.03 (s, 1H), 7.71 (d, J=2.4 Hz, 1H), 7.63 (d, J=8.2 Hz, 2H), 7.51 (s, 1H), 7.09 (d, J=8.2 Hz, 2H), 6.60 (d, J=2.4 Hz, 1H), 5.59 (s, 2H), 4.16 (s, 2H), 3.97 (q, J=7.1 Hz, 2H), 3.88 (s, 3H), 1.23 (t, J=7.1 Hz, 3H). LCMS (method 2): R$_t$=1.474 min; HRMS (ESIpos): m/z [M+H]$^+$ calcd for C$_{24}$H$_{21}$ClN$_8$O$_2$S 521.1269. found, 521.1272.

Example 21: 7-benzyl-8-((2-chloroimidazo[2,1-b]thiazol-6-yl)methyl)-3-ethyl-3,7-dihydro-1H-purine-2,6-dione (KM-06-108)

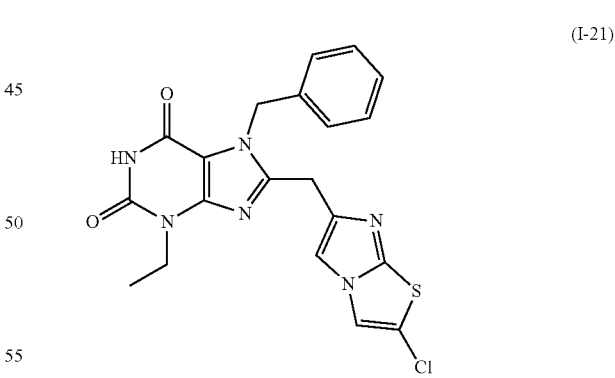

(I-21)

$^1$H NMR (300 MHz, DMSO-d$_6$) δ 11.10 (s, 1H), 8.10 (s, 1H), 7.54 (s, 1H), 7.28-7.24 (m, 2H), 7.23-7.20 (m, 1H), 7.10 (d, J=7.6 Hz, 2H), 5.60 (s, 2H), 4.13 (s, 2H), 3.96 (q, J=7.0 Hz, 2H), 1.22 (t, J=7.1 Hz, 3H). LCMS (method 2): R$_t$=1.555 min; HRMS (ESIpos): m/z [M+H]$^+$ calcd for C$_{20}$H$_{17}$ClN$_6$O$_2$S 441.0895. found, 441.0898.

Example 22: 7-benzyl-3-cyclopropyl-8-(imidazo[1,2-a]pyridin-2-ylmethyl)-3,7-dihydro-1H-purine-2,6-dione (KM-06-109)

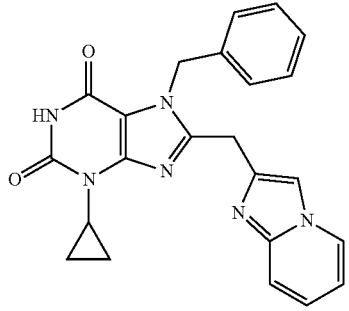

(I-22)

$^1$H NMR (300 MHz, DMSO-d$_6$) δ 11.03 (s, 1H), 8.42 (d, J=6.7 Hz, 1H), 7.70 (s, 1H), 7.47 (d, J=9.2 Hz, 1H), 7.27-7.23 (m, 2H), 7.22-7.18 (m, 2H), 7.14 (d, J=7.5 Hz, 2H), 6.86-6.83 (m, 1H), 5.62 (s, 2H), 4.22 (s, 2H), 2.92-2.86 (m, 1H), 1.04-0.99 (m, 2H), 0.99-0.95 (m, 2H). LCMS (method 2): R$_t$=1.097 min; HRMS (ESIpos): m/z [M+H]$^+$ calcd for C$_{23}$H$_{20}$N$_6$O$_2$ 413.1721. found, 413.1725.

Example 23: 3-ethyl-7-(4-(2-hydroxyethyl)benzyl)-8-(imidazo[1,2-a]pyridin-2-ylmethyl)-3,7-dihydro-1H-purine-2,6-dione (KM-06-111)

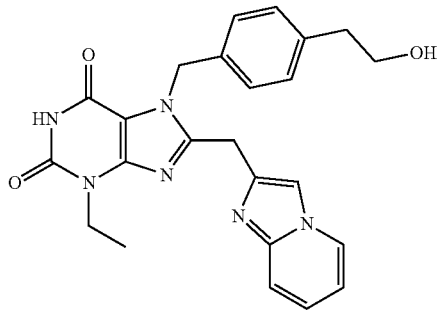

(I-23)

$^1$H NMR (600 MHz, DMSO-d$_6$) δ 11.11 (s, 1H), 8.42 (d, J=6.7 Hz, 1H), 7.68 (s, 1H), 7.47 (dd, J=9.2, 0.8 Hz, 1H), 7.20 (ddd, J=9.2, 6.7, 1.4 Hz, 1H), 7.12-7.06 (m, 4H), 6.86-6.83 (m, 1H), 5.57 (s, 2H), 4.60 (t, J=5.2 Hz, 1H), 4.23 (s, 2H), 3.96 (q, J=7.1 Hz, 2H), 3.54 (td, J=7.1, 5.0 Hz, 2H), 2.64 (t, J=7.1 Hz, 2H), 1.22 (t, J=7.1 Hz, 3H). LCMS (method 2): R$_t$=0.955 min; HRMS (ESIpos): m/z [M+H]$^+$ calcd for C$_{24}$H$_{24}$N$_6$O$_3$ 445.1983. found, 445.1986.

Example 24: 2-(4-((3-ethyl-8-(imidazo[1,2-a]pyridin-2-ylmethyl)-2,6-dioxo-1,2,3,6-tetrahydro-7H-purin-7-yl)methyl)phenyl)acetic Acid (KM-06-112)

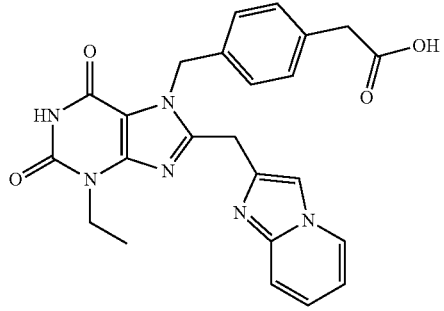

(I-24)

$^1$H NMR (600 MHz, DMSO-d$_6$) δ 11.11 (s, 1H), 8.43-8.40 (m, 1H), 7.68 (s, 1H), 7.47 (d, J=9.0 Hz, 1H), 7.20 (ddd, J=9.2, 6.7, 1.5 Hz, 1H), 7.15 (d, J=8.2 Hz, 2H), 7.12 (d, J=8.2 Hz, 2H), 6.86-6.83 (m, 1H), 5.60 (s, 2H), 4.24 (s, 2H), 3.96 (q, J=7.1 Hz, 2H), 3.49 (s, 2H), 1.22 (t, J=7.1 Hz, 3H). LCMS (method 2): R$_t$=1.022 min; HRMS (ESIpos): m/z [M+H]$^+$ calcd for C$_{24}$H$_{22}$N$_6$O$_4$ 459.1775. found, 459.1775.

Example 25: benzyl-8-(imidazo[1,2-a]pyridin-2-ylmethyl)-3-propyl-3,7-dihydro-1H-purine-2,6-dione (KM-06-113)

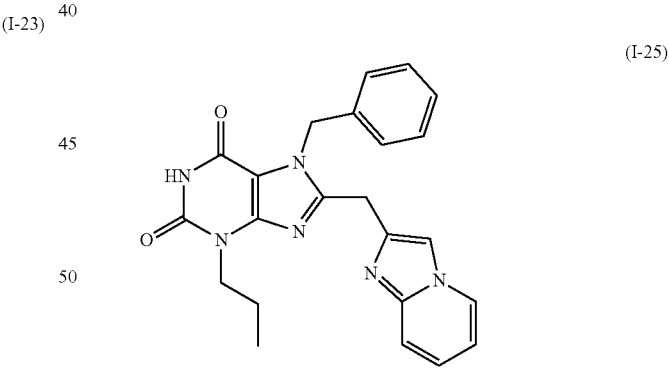

(I-25)

$^1$H NMR (600 MHz, DMSO-d$_6$) δ 11.12 (s, 1H), 8.43-8.39 (m, 1H), 7.69 (s, 1H), 7.48-7.44 (m, 1H), 7.26 (ddd, J=7.5, 6.2, 1.4 Hz, 2H), 7.23-7.18 (m, 2H), 7.16-7.12 (m, 2H), 6.86-6.82 (m, 1H), 5.62 (s, 2H), 4.23 (s, 2H), 3.91-3.86 (m, 2H), 1.73-1.65 (m, 2H), 0.89 (t, J=7.5 Hz, 3H). LCMS (method 2): R$_t$=1.163 min; HRMS (ESIpos): m/z [M+H]$^+$ calcd for C$_{23}$H$_{22}$N$_6$O$_4$ 415.1877. found, 415.1874.

Example 26: 3-ethyl-7-(4-fluorobenzyl)-8-((2-methylimidazo[2,1-b]thiazol-6-yl)methyl)-3,7-dihydro-1H-purine-2,6-dione (KM-06-114)

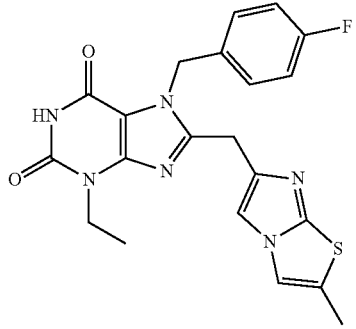

(I-26)

$^1$H NMR (600 MHz, DMSO-d$_6$) δ 11.10 (s, 1H), 7.53 (q, J=1.5 Hz, 1H), 7.44 (s, 1H), 7.19-7.15 (m, 2H), 7.09-7.05 (m, 2H), 5.57 (s, 2H), 4.11 (s, 2H), 3.96 (q, J=7.0 Hz, 2H), 2.37 (d, J=1.4 Hz, 3H), 1.22 (t, J=7.1 Hz, 3H). LCMS (method 2): R$_t$=1.333 min; HRMS (ESIpos): m/z [M+H]$^+$ calcd for C$_{21}$H$_{19}$FN$_6$O$_2$S 439.1347. found, 439.1356.

Example 27: 3-ethyl-7-(4-methoxybenzyl)-8-((2-methylimidazo[2,1-b]thiazol-6-yl)methyl)-3,7-dihydro-1H-purine-2,6-dione (KM-06-115)

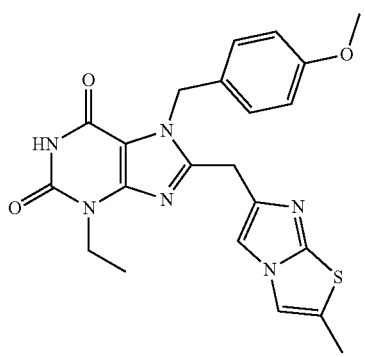

(I-27)

$^1$H NMR (600 MHz, DMSO-d$_6$) δ 11.09 (s, 1H), 7.54 (q, J=1.5 Hz, 1H), 7.43 (s, 1H), 7.11 (d, J=8.7 Hz, 2H), 6.82 (d, J=8.7 Hz, 2H), 5.52 (s, 2H), 4.10 (s, 2H), 3.95 (q, J=7.1 Hz, 2H), 3.70 (s, 3H), 2.37 (d, J=1.3 Hz, 3H), 1.21 (t, J=7.1 Hz, 3H). LCMS (method 2): R$_t$=1.272 min; HRMS (ESIpos): m/z [M+H]$^+$ calcd for C$_{22}$H$_{22}$N$_6$O$_3$S 451.1547. found, 451.1546.

Example 28: N-(4-((8-((2-chloroimidazo[2,1-b]thiazol-6-yl)methyl)-3-ethyl-1,2,3,6-tetrahydro-2,6-dioxopurin-7-yl)methyl)phenyl)acetamide (KM-06-148)

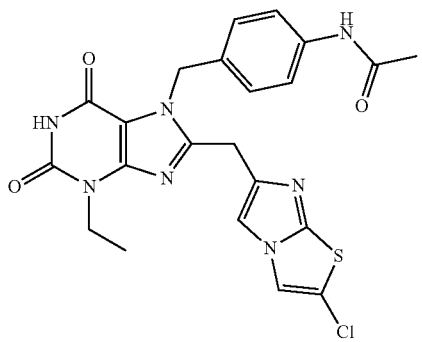

(I-28)

$^1$H NMR (300 MHz, DMSO-d$_6$) δ 11.12 (s, 1H), 9.90 (s, 1H), 8.03 (s, 1H), 7.50 (s, 1H), 7.44 (d, J=8.5 Hz, 2H), 7.01 (d, J=8.5 Hz, 2H), 5.50 (s, 2H), 4.13 (s, 2H), 3.94 (q, J=7.1 Hz, 2H), 2.01 (s, 3H), 1.20 (t, J=7.0 Hz, 3H). LCMS (method 2): R$_t$=1.314 min; HRMS (ESIpos): m/z [M+H]$^+$ calcd for C$_{22}$H$_{20}$ClN$_7$O$_3$S 498.1110. found, 498.1112.

Example 29: 7-(4-(1H-1,2,4-triazol-1-yl)benzyl)-8-((2-chloroimidazo[2,1-b]thiazol-6-yl)methyl)-3-ethyl-3,7-dihydro-1H-purine-2,6-dione (KM-06-149)

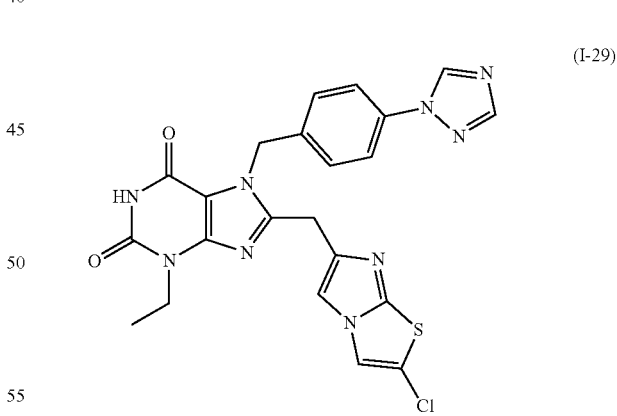

(I-29)

$^1$H NMR (300 MHz, DMSO-d$_6$) δ 11.14 (s, 1H), 9.21 (s, 1H), 8.21 (s, 1H), 7.98 (s, 1H), 7.66 (d, J=8.5 Hz, 2H), 7.46 (s, 1H), 7.14 (d, J=8.5 Hz, 2H), 5.62 (s, 2H), 4.19 (s, 2H), 3.97 (q, J=6.6 Hz, 2H), 1.23 (t, J=7.0 Hz, 3H). LCMS (method 2): R$_t$=1.348 min; HRMS (ESIpos): m/z [M+H]$^+$ calcd for C$_{22}$H$_{16}$ClN$_9$O$_2$S 508.1065. found, 508.1069.

Example 30: N-(4-((3-ethyl-8-((2-methylimidazo[2,1-b]thiazol-6-yl)methyl)-2,6-dioxo-1,2,3,6-tetrahydro-7H-purin-7-yl)methyl)phenyl)acetamide (KM-06-150)

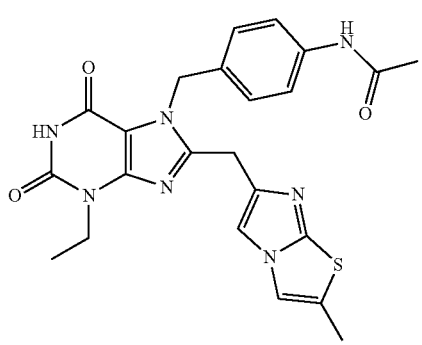

(I-30)

$^1$H NMR (300 MHz, DMSO-d$_6$) δ 11.11 (s, 1H), 9.92 (s, 1H), 7.52 (s, 1H), 7.50-7.42 (m, 3H), 7.07 (d, J=8.5 Hz, 2H), 5.52 (s, 2H), 4.08 (s, 2H), 3.94 (q, J=7.1 Hz, 2H), 2.35 (s, 3H), 2.02 (s, 3H), 1.20 (t, J=7.1 Hz, 3H). LCMS (method 2): R$_t$=1.101 min; HRMS (ESIpos): m/z [M+H]$^+$ calcd for C$_{23}$H$_{23}$N$_7$O$_3$S 478.1656. found, 478.1662.

Example 31: 7-(4-(1H-1,2,4-triazol-1-yl)benzyl)-3-ethyl-8-((5,6,7,8-tetrahydroimidazo[1,2-a]pyridin-2-yl)methyl)-3,7-dihydro-1H-purine-2,6-dione (KM-06-151)

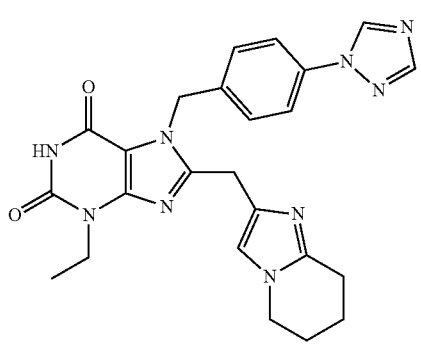

(I-31)

$^1$H NMR (300 MHz, DMSO-d$_6$) δ 11.12 (s, 1H), 9.26 (s, 1H), 8.23 (s, 1H), 7.76 (d, J=8.6 Hz, 2H), 7.23 (d, J=8.6 Hz, 2H), 6.67 (s, 1H), 5.63 (s, 2H), 4.01-3.91 (m, 4H), 3.70 (t, J=5.6 Hz, 2H), 2.55 (t, J=6.0 Hz, 2H), 1.75-1.64 (m, 4H), 1.22 (t, J=7.1 Hz, 3H). LCMS (method 2): R$_t$=0.951 min; HRMS (ESIpos): m/z [M+H]$^+$ calcd for C$_{24}$H$_{26}$N$_9$O$_2$ 472.2204. found, 472.2210.

Example 32: 3-ethyl-8-((2-methylimidazo[2,1-b]thiazol-6-yl)methyl)-7-(4-(2-oxopyrrolidin-1-yl)benzyl)-3,7-dihydro-1H-purine-2,6-dione (KM-06-153)

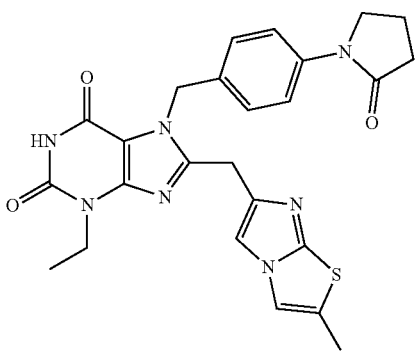

(I-32)

$^1$H NMR (300 MHz, DMSO-d$_6$) δ 11.12 (s, 1H), 7.52 (d, J=8.6 Hz, 3H), 7.41 (s, 1H), 7.11 (d, J=8.7 Hz, 2H), 5.55 (s, 2H), 4.09 (s, 2H), 3.94 (q, J=7.0 Hz, 2H), 3.75 (t, J=7.0 Hz, 2H), 2.49-2.43 (m, 2H), 2.34 (s, 3H), 2.10-1.97 (m, 2H), 1.20 (t, J=7.1 Hz, 3H). LCMS (method 2): R$_t$=1.218 min; HRMS (ESIpos): m/z [M+H]$^+$ calcd for C$_{25}$H$_{25}$N$_7$O$_3$S 504.1812. found, 504.1813.

Example 33: 7-(4-(1H-imidazol-1-yl)benzyl)-3-ethyl-8-((5,6,7,8-tetrahydroimidazo[1,2-a]pyridin-2-yl)methyl)-3,7-dihydro-1H-purine-2,6-dione (KM-06-156)

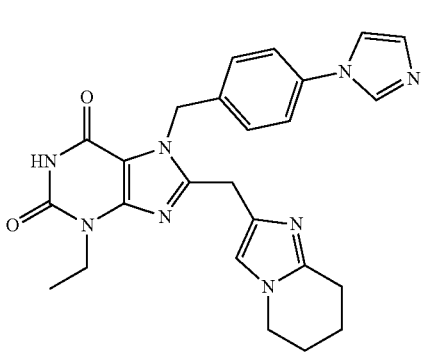

(I-33)

$^1$H NMR (300 MHz, DMSO-d$_6$) δ 11.12 (s, 1H), 8.22 (s, 1H), 7.71 (s, 1H), 7.57 (d, J=8.5 Hz, 2H), 7.21 (d, J=8.5 Hz, 2H), 7.10 (s, 1H), 6.69 (s, 1H), 5.62 (s, 2H), 4.00-3.91 (m, 4H), 3.73 (t, J=5.6 Hz, 2H), 2.57 (t, J=6.0 Hz, 2H), 1.80-1.64 (m, 4H), 1.22 (t, J=7.1 Hz, 3H). LCMS (method 2): R$_t$=0.122 min; HRMS (ESIpos): m/z [M+H]$^+$ calcd for C$_{25}$H$_{26}$N$_8$O$_2$ 471.2251 found, 471.2256.

Example 34: 8-((2-chloroimidazo[2,1-b]thiazol-6-yl)methyl)-7-(4-(3,3-difluoroazetidin-1-yl)benzyl)-3-ethyl-3,7-dihydro-1H-purine-2,6-dione (KM-06-160)

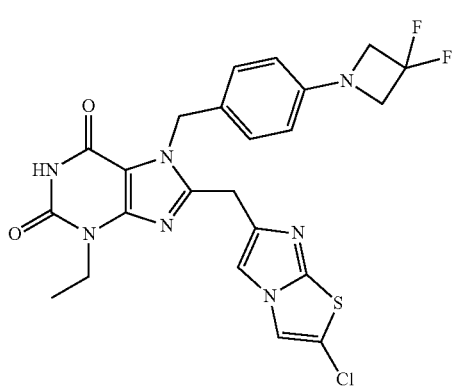

(I-34)

$^1$H NMR (300 MHz, DMSO-d$_6$) δ 11.12 (s, 1H), 8.11 (s, 1H), 7.48 (s, 1H), 7.02 (d, J=8.2 Hz, 2H), 6.41 (d, J=8.2 Hz, 2H), 5.46 (s, 2H), 4.23-4.21 (m, 1H), 4.18 (s, 2H), 4.15-4.13 (m, 3H), 3.93 (q, J=6.8 Hz, 2H), 1.19 (t, J=6.9 Hz, 3H). LCMS (method 2): R$_t$=1.667 min; HRMS (ESIpos): m/z [M+H]$^+$ calcd for C23H20ClF2N7O2S 532.1129. found, 532.1127.

Example 35: N-(4-((3-ethyl-2,6-dioxo-8-((5,6,7,8-tetrahydroimidazo[1,2-a]pyridin-2-yl)methyl)-1,2,3,6-tetrahydro-7H-purin-7-yl)methyl)phenyl)acetamide (KM-06-163)

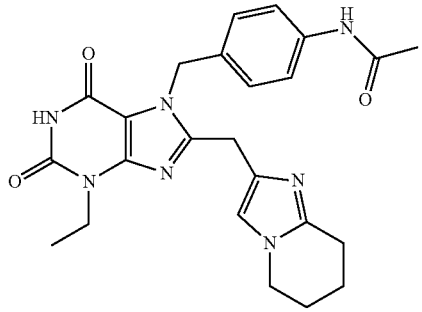

(I-35)

$^1$H NMR (300 MHz, DMSO-d$_6$) δ 11.10 (s, 1H), 9.96 (s, 1H), 7.48 (d, J=8.5 Hz, 2H), 7.05 (d, J=8.5 Hz, 2H), 6.68 (s, 1H), 5.52 (s, 2H), 3.99-3.87 (m, 4H), 3.76 (t, J=5.7 Hz, 2H), 2.60 (t, J=6.1 Hz, 2H), 2.02 (s, 3H), 1.85-1.71 (m, 4H), 1.20 (t, J=7.1 Hz, 3H). LCMS (method 2): R$_t$=0.575 min; HRMS (ESIpos): m/z [M+H]$^+$ calcd for C$_{24}$H$_{27}$N$_7$O$_3$ 462.2248. found, 462.2257.

Example 36: 3-ethyl-7-(4-(2-oxopyrrolidin-1-yl)benzyl)-8-((5,6,7,8-tetrahydroimidazo[1,2-a]pyridin-2-yl)methyl)-3,7-dihydro-1H-purine-2,6-dione (KM-06-164)

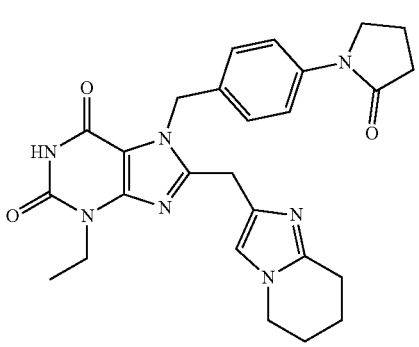

(I-36)

$^1$H NMR (300 MHz, DMSO-d$_6$) δ 11.10 (s, 1H), 7.57 (d, J=8.7 Hz, 2H), 7.12 (d, J=8.7 Hz, 2H), 6.70 (s, 1H), 5.56 (s, 2H), 3.97-3.87 (m, 4H), 3.82-3.73 (m, 4H), 2.60 (t, J=6.1 Hz, 2H), 2.46 (d, J=8.3 Hz, 2H), 2.09-2.00 (m, 2H), 1.85-1.71 (m, 4H), 1.20 (t, J=7.4 Hz, 3H). LCMS (method 2): R$_t$=1.063 min; HRMS (ESIpos): m/z [M+H]$^+$ calcd for C$_{26}$H$_{29}$N$_7$O$_3$ 488.2405 found, 488.2407.

Example 37: 7-(4-(3,3-difluoroazetidin-1-yl)benzyl)-3-ethyl-8-((5,6,7,8-tetrahydroimidazo[1,2-a]pyridin-2-yl)methyl)-3,7-dihydro-1H-purine-2,6-dione (KM-06-165)

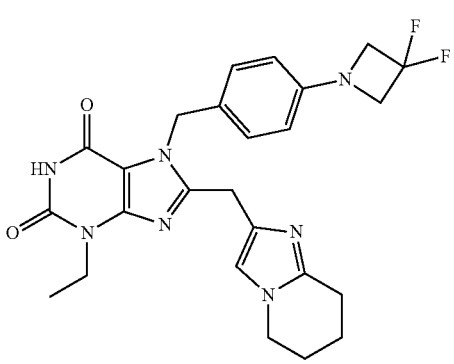

(I-37)

$^1$H NMR (300 MHz, DMSO-d$_6$) δ 11.09 (s, 1H), 7.09 (d, J=8.6 Hz, 2H), 6.72 (s, 1H), 6.50 (d, J=8.6 Hz, 2H), 5.49 (s, 2H), 4.23 (t, J=12.4 Hz, 4H), 3.98-3.88 (m, 4H), 3.81 (t, J=5.8 Hz, 2H), 2.64 (t, J=6.1 Hz, 2H), 1.87-1.74 (m, 4H), 1.19 (t, J=7.1 Hz, 3H). LCMS (method 2): R$_t$=1.251 min; HRMS (ESIpos): m/z [M+H]$^+$ calcd for C$_{25}$H$_{27}$F$_2$N$_7$O$_2$ 496.2267. found, 496.2274.

Example 38: 3-ethyl-7-(4-(3-methoxyazetidin-1-yl)benzyl)-8-((5,6,7,8-tetrahydroimidazo[1,2-a]pyridin-2-yl)methyl)-3,7-dihydro-1H-purine-2,6-dione (KM-06-176)

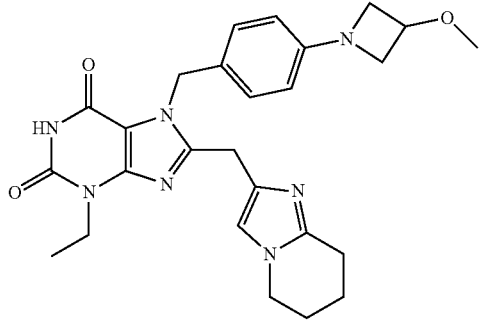

(I-38)

$^1$H NMR (300 MHz, DMSO-d$_6$) δ 11.09 (s, 1H), 7.04 (d, J=8.5 Hz, 2H), 6.70 (s, 1H), 6.37 (d, J=8.5 Hz, 2H), 5.46 (s, 2H), 4.29 (ddd, J=10.4, 6.0, 4.2 Hz, 1H), 4.00 (t, J=7.2 Hz, 2H), 3.97-3.87 (m, 4H), 3.81 (t, J=5.7 Hz, 2H), 3.54 (dd, J=8.3, 4.4 Hz, 2H), 3.22 (s, 3H), 2.64 (t, J=6.1 Hz, 2H), 1.88-1.74 (m, 4H), 1.19 (t, J=7.0 Hz, 3H). LCMS (method 2): R$_t$=1.149 min; HRMS (ESIpos): m/z [M+H]$^+$ calcd for C$_{26}$H$_{31}$N$_7$O$_3$ 490.2561. found, 490.2558.

Example 39: 3-ethyl-7-(4-(5-methyl-1,2,4-oxadiazol-3-yl)benzyl)-8-((5,6,7,8-tetrahydroimidazo[1,2-a]pyridin-2-yl)methyl)-3,7-dihydro-1H-purine-2,6-dione (KM-06-180)

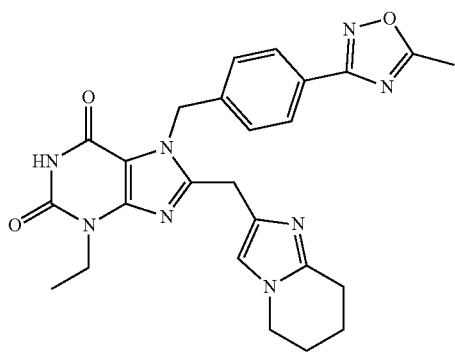

(I-39)

$^1$H NMR (300 MHz, DMSO-d$_6$) δ 11.11 (s, 1H), 7.89 (d, J=8.5 Hz, 2H), 7.19 (d, J=8.5 Hz, 2H), 6.65 (s, 1H), 5.66 (s, 2H), 4.01-3.91 (m, 4H), 3.68 (t, J=5.4 Hz, 2H), 2.66 (s, 3H), 2.57-2.52 (m, 2H), 1.77-1.64 (m, 4H), 1.23 (t, J=7.1 Hz, 3H). LCMS (method 2): R$_t$=1.144 min; HRMS (ESIpos): m/z [M+H]$^+$ calcd for C$_{25}$H$_{26}$N$_8$O$_3$ 487.2201. found, 487.2194.

In Vitro Enzyme Activity Assay

These compounds according to the aforementioned examples were tested for tryptophan hydroxylase (TPH) inhibitory activity in a fluorescence-based in vitro assay, using recombinant human TPH1 (Swiss-Prot: P17752) and TPH2 (Swiss-Prot: Q8IWU9).

The full-length coding sequences of human TPH1 and TPH2 were PCR amplified, ligated into a MBP fusion vector (pMalc2x, New England Biolabs, MA, USA) and transformed into SCS1 (Stratagene, CA, USA) to amplify plasmid DNA. For the overexpression of TPH proteins, the constructs were transformed into Rosetta (DE3) (Novagen®/EMD Millipore, MA, USA) and cultivated in terrific broth (TB) medium (AppliChem, Darmstadt, Germany) at 37° C. When the bacterial cultures reached an OD600≈2, expression was induced with 0.5 mM IPTG (AppliChem, Darmstadt, Germany) over night at 17° C. The purification of soluble proteins started with sonication-mediated cell disruption in lysis buffer (1×PBS pH 7.4, 0.5 M NaCl, 5 Glycerol+CHAPS, DTT, PMSF, benzonase), followed by affinity purification (MBPTrap, GE Healthcare, UK) and gel filtration (26/60 Superdex 200 prep grade, GE Healthcare, UK), according to the manufacturer's protocol. The quality of protein expression and solubility was controlled by SDS-PAGE and Coomassie blue staining.

The enzymatic reaction was carried out in black 96-well flat bottom plates (Corning GmbH, Wiesbaden). TPH1 and TPH2 activities were measured in a reaction mixture containing 50 mM 4-Morpholineethanesulfonic acid (MES), pH 7.0, 40 µM tryptophan, 200 mM ammonium sulfate, 25 µM ferrous ammonium sulfate, 50 µM tetrahydrobiopterin, 25 µg/ml catalase, and 7 mM DTT. The reactions were initiated by adding TPH1 or TPH2 to a final concentration of 5 µg/ml. Initial velocity of the reactions was determined by following the change of fluorescence at 330 nm (excitation wavelength=300 nm) (Infinite M200, Tecan, Crailsheim).

TPH1 and TPH2 inhibition was determined by measuring a compound dose response, using a serial dilution of a 5 mM DMSO stock solution. The potency of a given compound was calculated in GraphPad PRISM 6 software (San Diego, USA) with a Nonlinear Regression fit (log(inhibitor) vs. response-variable slope) using the relative fluorescence units (RFU) of the sample triplicates.

For comparative reasons, the TPH1 and TPH2 inhibition was tested under the same experimental condition with the inhibitors (LX1606 obtained from AdooQ BioScience, Irvine, Calif., USA), LX1031 (obtained from ApexBio Technology, Houston, Tex., USA) and LP533401 (obtained from Dalton Pharma Services, Toronto, CANADA).

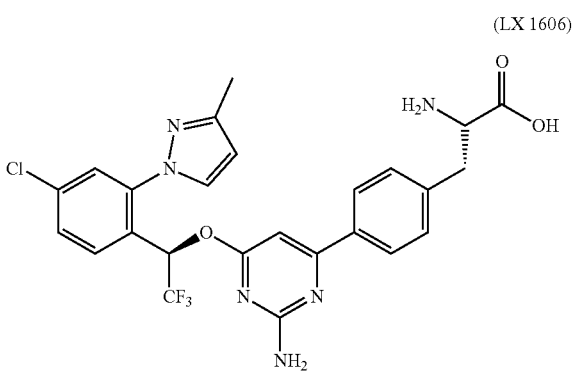

(LX 1606)

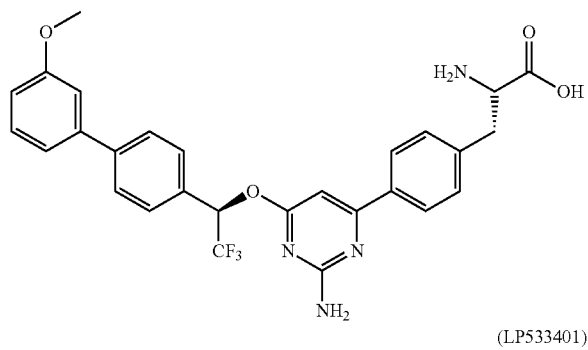
(LX1031)

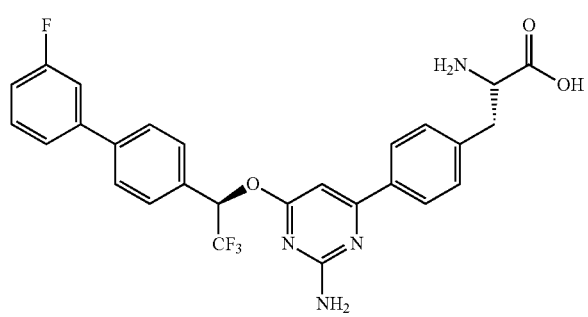
(LP533401)

The results for the inhibition of TPH1 and TPH2 are shown in Tables 1 and 2, respectively.

TABLE 1

Inhibition of TPH1

| IC$_{50}$ TPH1 (µM) | | compound (Example Nr./Lab- |
|---|---|---|
| mean | sd | Journal/Internal Ref.) |
| 0.770 | 0.060 | Ex. 1/KM-06-30/(I-1) |
| 0.412 | 0.143 | Ex. 2/KM-06-57/(I-2) |
| 0.338 | 0.169 | Ex. 3/KM-06-70/(I-3) |
| 0.198 | 0.022 | Ex. 4/KM-06-78/(I-4) |
| 0.409 | 0.093 | Ex. 5/KM-06-79/(I-5) |
| 7.827 | 0.822 | Ex. 6/KM-06-80/(I-6) |
| 0.177 | 0.033 | Ex. 7/KM-06-81/(I-7) |
| 0.219 | 0.051 | Ex. 8/KM-06-82/(I-8) |
| 0.288 | 0.025 | Ex. 9/KM-06-89/(I-9) |
| 0.232 | 0.018 | Ex. 10/KM-06-90/(I-10) |
| 0.940 | 0.179 | Ex. 11/KM-06-91/(I-11) |
| 0.487 | 0.081 | Ex. 12/KM-06-93/(I-12) |
| 0.213 | 0.091 | Ex. 13/KM-06-66/(I-13) |
| 0.068 | 0.008 | Ex. 14/KM-06-64/(I-14) |
| 0.034 | 0.008 | Ex. 15/KM-06-96/(I-15) |
| 0.054 | 0.007 | Ex. 16/KM-06-97/(I-16) |
| 0.084 | 0.022 | Ex. 17/KM-06-98/(I-17) |
| 0.209 | 0.004 | Ex. 18/KM-06-99/(I-18) |
| 0.763 | 0.062 | Ex. 19/KM-06-106/(I-19) |
| 0.225 | 0.056 | Ex. 20/KM-06-107/(I-20) |
| 0.162 | 0.006 | Ex. 21/KM-06-108/(I-21) |
| 0.802 | 0.096 | Ex. 22/KM-06-109/(I-22) |
| 2.060 | 0.254 | Ex. 23/KM-06-111/(I-23) |
| 133.6 | 45.54 | Ex. 24/KM-06-112/(I-24) |
| 0.758 | 0.020 | Ex. 25/KM-06-113/(I-25) |
| 0.217 | 0.025 | Ex. 26/KM-06-114/(I-26) |
| 0.133 | 0.017 | Ex. 27/KM-06-115/(I-27) |
| 0.116 | 0.012 | Ex. 28/KM-06-148/(I-28) |
| 0.419 | 0.039 | Ex. 29/KM-06-149/(I-29) |
| 0.056 | 0.009 | Ex. 30/KM-06-150/(I-30) |
| 0.469 | 0.072 | Ex. 31/KM-06-151/(I-31) |
| 0.069 | 0.015 | Ex. 32/KM-06-153/(I-32) |
| 0.546 | 0.358 | Ex. 33/KM-06-156/(I-33) |
| 0.411 | 0.282 | Ex. 34/KM-06-160/(I-34) |

TABLE 1-continued

Inhibition of TPH1

| IC$_{50}$ TPH1 (µM) | | compound (Example Nr./Lab- |
|---|---|---|
| mean | sd | Journal/Internal Ref.) |
| 0.286 | 0.039 | Ex. 35/KM-06-163/(I-35) |
| 0.247 | 0.034 | Ex. 36/KM-06-164/(I-36) |
| 0.273 | 0.034 | Ex. 37/KM-06-165/(I-37) |
| 0.220 | 0.017 | Ex. 38/KM-06-176/(I-38) |
| 0.179 | 0.011 | Ex. 39/KM-06-180/(I-39) |
| 0.77 | 0.09 | LX1606 (comparative Example) |
| 1.42 | 0.32 | LX1031 (comparative Example) |
| 2.01 | 0.56 | LP533401 (comparative Example) |

TABLE 2

Inhibition of TPH2

| IC$_{50}$ TPH2 (µM) | | compound (Example Nr./Lab- |
|---|---|---|
| mean | sd | Journal/Internal Ref.) |
| 0.043 | 0.012 | Ex. 1/KM-06-30/(I-1) |
| 0.040 | 0.005 | Ex. 2/KM-06-57/(I-2) |
| 0.039 | 0.019 | Ex. 3/KM-06-70/(I-3) |
| 0.020 | 0.002 | Ex. 4/KM-06-78/(I-4) |
| 0.030 | 0.003 | Ex. 5/KM-06-79/(I-5) |
| 0.272 | 0.044 | Ex. 6/KM-06-80/(I-6) |
| 0.017 | 0.002 | Ex. 7/KM-06-81/(I-7) |
| 0.018 | 0.004 | Ex. 8/KM-06-82/(I-8) |
| 0.020 | 0.001 | Ex. 9/KM-06-89/(I-9) |
| 0.017 | 0.001 | Ex. 10/KM-06-90/(I-10) |
| 0.076 | 0.031 | Ex. 11/KM-06-91/(I-11) |
| 0.020 | 0.003 | Ex. 12/KM-06-93/(I-12) |
| 0.018 | 0.003 | Ex. 13/KM-06-66/(I-13) |
| 0.011 | 0.001 | Ex. 14/KM-06-64/(I-14) |
| 0.014 | 0.003 | Ex. 15/KM-06-96/(I-15) |
| 0.016 | 0.003 | Ex. 16/KM-06-97/(I-16) |
| 0.021 | 0.005 | Ex. 17/KM-06-98/(I-17) |
| 0.030 | 0.003 | Ex. 18/KM-06-99/(I-18) |
| 0.038 | 0.001 | Ex. 19/KM-06-106/(I-19) |
| 0.024 | 0.010 | Ex. 20/KM-06-107/(I-20) |
| 0.015 | 0.004 | Ex. 21/KM-06-108/(I-21) |
| 0.061 | 0.009 | Ex. 22/KM-06-109/(I-22) |
| 0.071 | 0.021 | Ex. 23/KM-06-111/(I-23) |
| 3.11 | 0.31 | Ex. 24/KM-06-112/(I-24) |
| 0.045 | 0.016 | Ex. 25/KM-06-113/(I-25) |
| 0.039 | 0.001 | Ex. 26/KM-06-114/(I-26) |
| 0.025 | 0.003 | Ex. 27/KM-06-115/(I-27) |
| 0.017 | 0.002 | Ex. 28/KM-06-148/(I-28) |
| 0.023 | 0.005 | Ex. 29/KM-06-149/(I-29) |
| 0.016 | 0.001 | Ex. 30/KM-06-150/(I-30) |
| 0.031 | 0.001 | Ex. 31/KM-06-151/(I-31) |
| 0.017 | 0.002 | Ex. 32/KM-06-153/(I-32) |
| 0.029 | 0.003 | Ex. 33/KM-06-156/(I-33) |
| 0.096 | 0.038 | Ex. 34/KM-06-160/(I-34) |
| 0.036 | 0.003 | Ex. 35 /KM-06-163/(I-35) |
| 0.030 | 0.004 | Ex. 36/KM-06-164/(I-36) |
| 0.032 | 0.002 | Ex. 37/KM-06-165/(I-37) |
| 0.035 | 0.004 | Ex. 38/KM-06-176/(I-38) |
| 0.026 | 0.004 | Ex. 39/KM-06-180/(I-39) |
| 0.73 | 0.10 | LX1606 (comparative Example) |
| 1.63 | 0.31 | LX1031 (comparative Example) |
| 2.23 | 0.50 | LP533401 (comparative Example) |

The data show that the xanthine derivatives according to the invention have an inhibiting effect with respect to the enzymatic activity of TPH1 and TPH2 which is at least comparable to the known compounds LX1606 and LP533401, whereas several of the xanthine derivatives according to the invention even have a superior inhibiting effect over the known compounds.

The invention claimed is:

1. A method for treating a serotonin-related disease or disorder comprising administering to a patient in need thereof an effective amount of a compound or a pharmaceutically acceptable salt thereof, wherein the serotonin-related disease or disorder is Crohn's disease, ulcerative colitis, inflammatory bowel disease, or systemic sclerosis, and wherein the compound has the Formula (I):

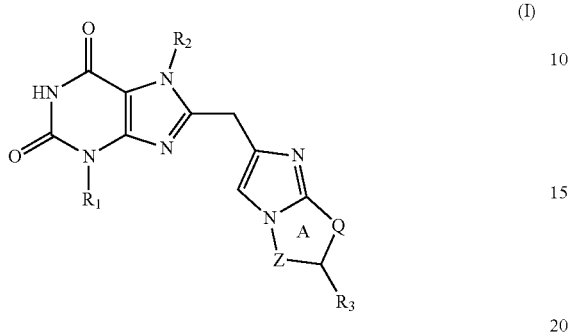

wherein:
$R^1$ and $R^2$ are each an optionally substituted group independently selected from the group consisting of a hydrogen (—H), one of a (C1-C10)-alkyl group, a (C2-C10)-alkenyl group, a (C2-C10)-alkynyl group, a (C6-C14)-aryl group, a (C6-C14)-heteroaryl group, a (C7-C15)-alkyl-arylene group, a (C7-C15)-alkyl-heteroarylene group, a (C8-C15)-alkenyl-arylene group, a (C8-C15)-alkenyl-heteroarylene group, a (C8-C15)-alkynyl-arylene group, a (C8-C15)-alkynyl-heteroarylene group, a (C7-C15)-aryl-alkylene group, a (C7-C15)-heteroaryl-alkylene group, a (C8-C15)-aryl-alkenylene group, a (C8-C15)-heteroaryl-alkenylene group, a (C8-C15)-aryl-alkynylene group, and a (C8-C15)-heteroaryl-alkynylene group, wherein alkyl, alkenyl, alkynyl, alkylene, alkenylene, and alkynylene, when present in the aforementioned groups, may comprise one or more bivalent groups substituting a carbon moiety —C— and the one or more bivalent groups is selected from the group consisting of —O—, —S—, —S(O)—, —SO$_2$—, —N=, —C(O)—, —C(O)O—, —OC(O)—, —C(O)N(R)—, —N(R)C(O)—, —OC(O)N(R)—, —N(R)C(O)O—, —N(R)C(O)N(R)—, (C3-C12)-heterocyclic alkylene, and (C3-C12)-heterocyclic alkenylene;

$R^3$ is a group independently selected from the group consisting of hydrogen (—H), fluoro (—F), bromo (—Br), chloro (—Cl), a hydroxyl group (—OH), an acyl group (—C(O)R), a carboxyl group (—C(O)OH), a carboxy ester group (—CO$_2$R), an alkoxy group (—OR), an aldehyde group (—C(O)H), a trihalide methyl ester group (—OCX$_3$), a primary amine group (—NH$_2$), a secondary amine group (—N(R)H), a tertiary amine group (—NR(R')), an amide group (—N(R)—C(O)—R), an imide group (—C(O)—N(R)—C(O)—R'), a carbamate group (—N(R)—C(O)—OR'), a carboxamide group (—C(O)N(R)R'), a carbimide group (—N(R)—C(O)—N(R')R''), a primary ketimine group —C(R)=NH, a secondary ketimine group (—C(R)=NR'), a nitrile group (—CN), an isonitrile group (—NC), a nitroxy group (—ONO), a nitro group (—NO$_2$), a nitrate group (—ONO$_2$), a nitroso group (—NO), a cyanate group (—OCN), an isocyanate group (—NCO), a sulfhydryl group (—SH), a sulfide group (—SR), a sulfurtrihalide group (—SX$_3$), a sulfurpentahalide group (—SX$_5$), a sulfinyl group (—S(O)R), a sulfonyl group (—SO$_2$R), a sulfino group (—SO$_2$H), and a sulfo group (—SO$_3$H), or an optionally substituted and/or optionally linked group selected from the group consisting of a (C1-C10)-alkyl group, a (C2-C10)-alkenyl group, a (C2-C10)-alkynyl group, a (C6-C14)-aryl group, a (C6-C14)-heteroaryl group, a (C7-C15)-alkyl-arylene group, a (C7-C15)-alkyl-heteroarylene group, a (C8-C15)-alkenyl-arylene group, a (C8-C15)-alkenyl-heteroarylene group, a (C8-C15)-alkynyl-arylene group, a (C8-C15)-alkynyl-heteroarylene group, a (C7-C15)-aryl-alkylene group, a (C7-C15)-heteroaryl-alkylene group, a (C8-C15)-aryl-alkenylene group, a (C8-C15)-heteroaryl-alkenylene group, a (C8-C15)-aryl-alkynylene group, and a (C8-C15)-heteroaryl-alkynylene group, wherein alkyl, alkenyl, alkynyl, alkylene, alkenylene, or alkynylene, when present in the aforementioned groups of $R^3$, may comprise one or more bivalent groups substituting a carbon moiety —C— and the one or more bivalent groups is selected from the group consisting of —O—, —S—, —S(O)—, —SO$_2$—, —N=, —N(R)—, —C(O)—, —C(O)O—, —OC(O)—, —C(O)N(R)—, —N(R)C(O)—, —OC(O)N(R)—, —N(R)C(O)O—, —N(R)C(O)N(R)—, (C3-C12)-heterocyclic alkylene, and (C3-C12)-heterocyclic alkenylene, and wherein X is a halide;

Q is selected from the group consisting of hydrogenated carbon, non-hydrogenated carbon, hydrogenated nitrogen, and non-hydrogenated nitrogen, oxygen, sulfur, —*CH$_2$—CH(R''')—, —*CH=C(R''')—, —*CH$_2$—O—, and —*CH$_2$—N(R''')—, wherein:
R''' represents hydrogen, a methyl group, an ethyl group, a cyclopropyl group,
a —CH$_2$-cyclopropyl group, or a halogen; and
the carbon marked with an asterisk is covalently linked to the imidazole group set forth in Formula (I);

Z is selected from the group consisting of hydrogenated carbon, and non-hydrogenated carbon, hydrogenated nitrogen, non-hydrogenated nitrogen, oxygen and sulfur;

the ring member A is a saturated, unsaturated, or aromatic ring;

the substituents for the optionally substituted groups are selected from the group consisting of a fluoro (—F), a bromo (—Br), a chloro (—Cl), a hydroxyl group (—OH), a (C1-C3)-alkyl group, a (C2-C3)-alkenyl group, an acyl group (—C(O)R), a carboxyl group (—C(O)OH), a carboxylate group (—C(O)O$^-$), a carboxy ester group (—CO$_2$R), an alkoxy group (—OR), an aldehyde group (—C(O)H), a trihalide methyl ester group (—OCX$_3$), a primary amine group (—NH$_2$), a secondary amine group (—N(R)H), a tertiary amine group (—NR(R')), an amide group (—N(R)—C(O)—R), an imide group (—C(O)—N(R)—C(O)—R'), a carbamate group (—N(R)—C(O)—OR'), a carboxamide group (—C(O)N(R)(R')), a carbimide group (—N(R)—C(O)—N(R')R''), a primary ketimine group(—C(R)=NH), a secondary ketimine group (—C(R)=NR'), a nitrile group (—CN), an isonitrile group (—NC), a nitroxy group (—ONO), a nitro group (—NO$_2$), a nitrate group (—ONO$_2$), a nitroso group (—NO), a cyanate group (—OCN), an isocyanate group (—NCO), a sulfhydryl group (—SH), a sulfide group (—SR), a sulfurtrihalide group (—SX$_3$), a sulfurpentahalide group (—SX$_5$), a sulfinyl group (—S(O)R), a sulfonyl group (—SO$_2$R), a sulfino group (—SO₂H), a sulfo group (—SO₃H), and combinations thereof, and wherein X is a halide;

R is independently hydrogen, a (C1-C3)-alkyl group, or a (C2-C3)-alkenyl group;

R' is independently hydrogen, a (C1-C3)-alkyl group, or a (C2-C3)-alkenyl group; and R" is independently hydrogen, a (C1-C3)-alkyl group, or a (C2-C3)-alkenyl group.

2. The method according to claim 1, wherein the compound or a pharmaceutical acceptable salt thereof is administered to the patient in a pharmaceutical preparation.

3. The method according to claim 1, wherein at least one of $R^1$ and $R^2$ is not hydrogen.

4. The method according to claim 1, wherein $R^1$ is selected from the group consisting of an optionally substituted linear, branched, and cyclic (C1-C5)-alkyl group.

5. The method according to claim 1, wherein $R^2$ is selected from the group consisting of an optionally substituted (C5-C13)-aryl, (C5-C13)-heteroaryl, (C6-C13)-alkyl-arylene, (C6-C13)-alkyl-heteroarylene, (C6-C13)-alkenyl-arylene, (C6-C13)-alkenylheteroarylene, (C6-C13)-alkynyl-arylene, (C6-C13)-alkynyl-heteroarylene, (C6-C13)-aryl-alkylene, (C6-C13)-heteroaryl-alkylene, (C6-C13)-aryl-alkenylene, (C6-C13)-heteroaryl-alkenylene, (C6-C13)-aryl-alkynylene, and (C6-C13)-heteroaryl-alkynylene.

6. The method according to claim 1, wherein $R^2$ is a group defined by chemical formula (Ia)

—R⁵—Ar (Ia), wherein:

$R^5$ is (C0-C3)-alkylene, and

Ar is an optionally substituted (C5-C12)-aryl or (C5-C12)-heteroaryl.

7. The method according to claim 1, wherein:

$R^3$ is hydrogen, fluorine, chlorine, bromine, amine, amide, carbonitrile, optionally substituted (C1-C10)-alkyl, optionally substituted saturated or unsaturated(C5-C6)-heterocycle, optionally substituted (C2-C10)-alkenyl, or optionally substituted (C1-C5)-alkoxy; the optionally substituted (C1-C10)-alkyl, when present, optionally comprises one or more bivalent groups; and the optionally substituted (C2-C10)-alkenyl, when present, optionally comprises one or more bivalent groups.

8. The method according to claim 1, wherein Q is selected from the group consisting of ethylene (—CH2-CH2-), ethenylene (—CH═CH—), and sulfur (—S—).

9. The method according to claim 1, wherein Z is selected from the group consisting of hydrogenated carbon, non-hydrogenated carbon, hydrogenated nitrogen, and non-hydrogenated nitrogen.

10. The method according to claim 1, wherein the compound or a pharmaceutically acceptable salt thereof is selected from the group consisting of one of the compounds represented by chemical Formulas (I-1) to (I-39):

(I-1)

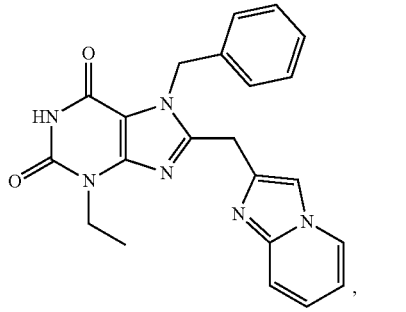

(I-2)

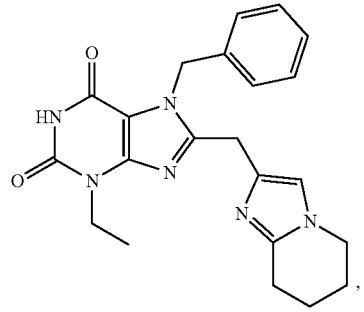

(I-3)

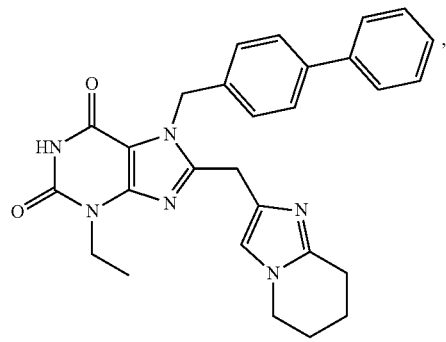

(I-4)

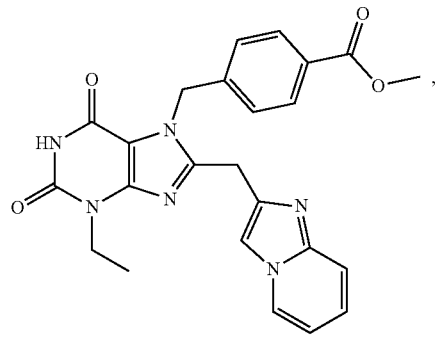

(I-5)

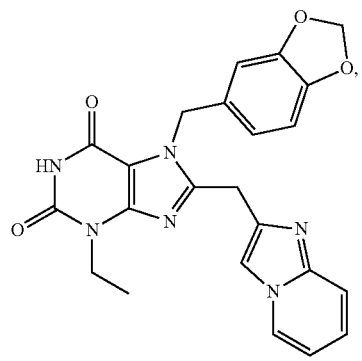

(I-6), (I-7), (I-8), (I-9), (I-10), (I-11), (I-12), (I-13)

(I-14)
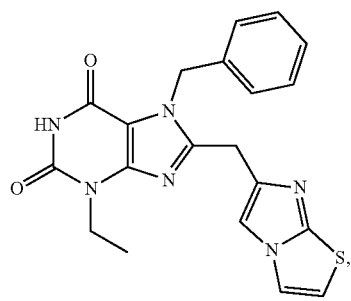
(I-15)
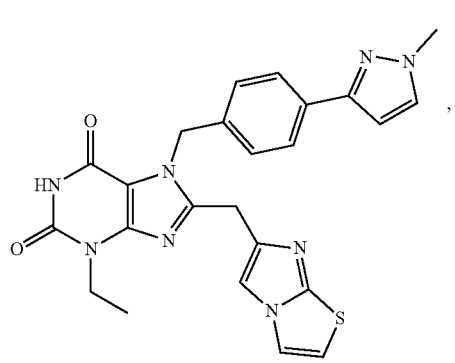
(I-16)
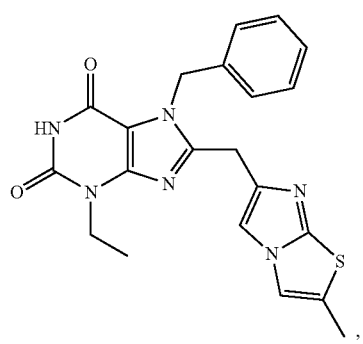
(I-17)
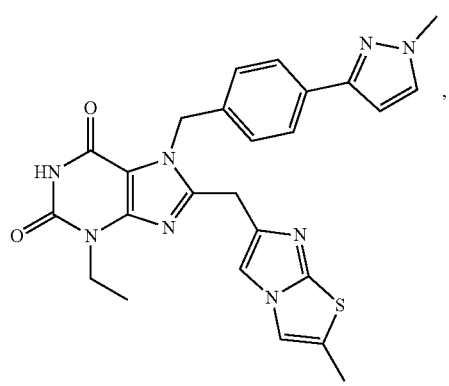
(I-18)
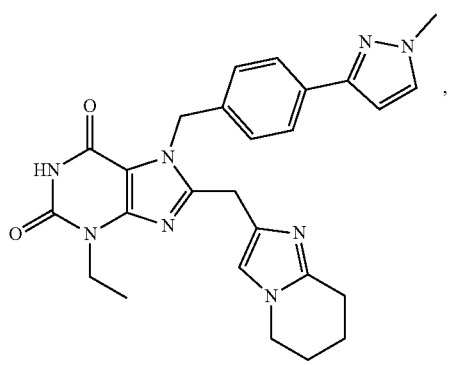
(I-19)
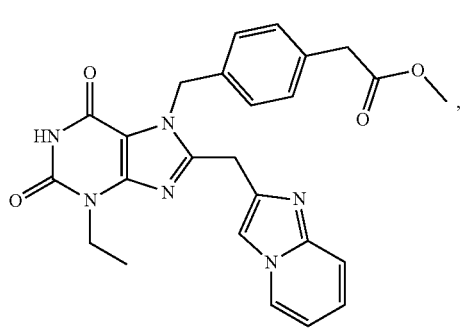
(I-20)
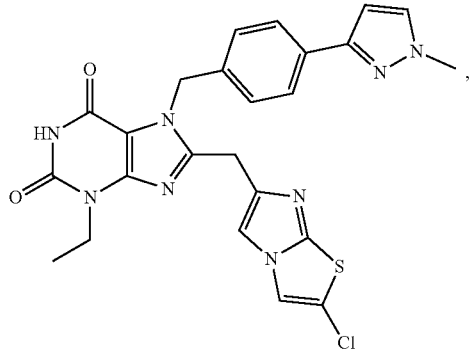
(I-21)
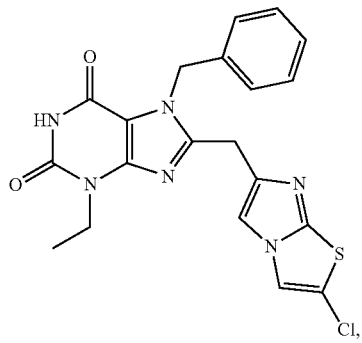

(I-22) 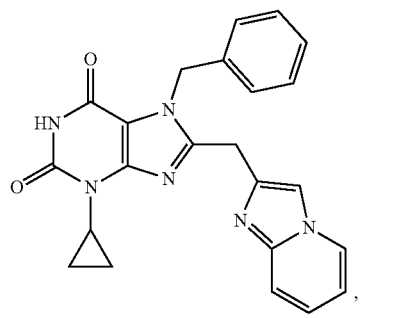
(I-23) 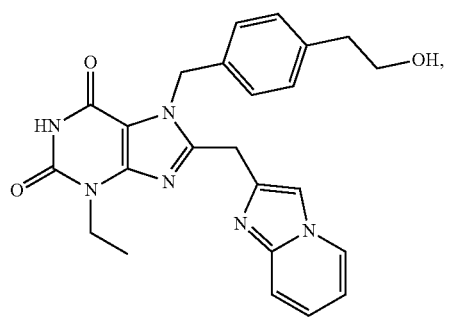
(I-24) 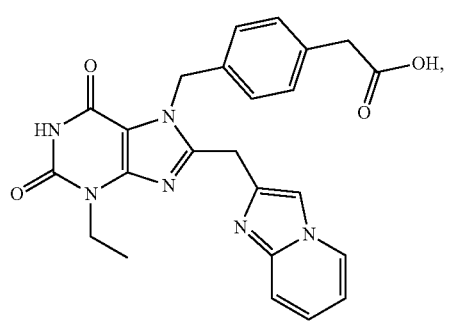
(I-25) 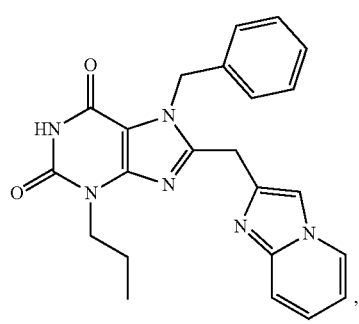
(I-26) 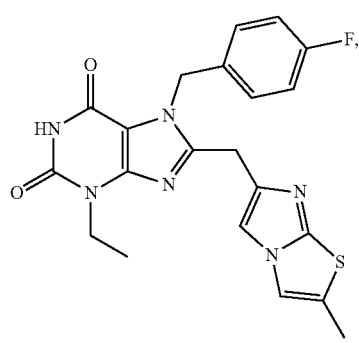
(I-27) 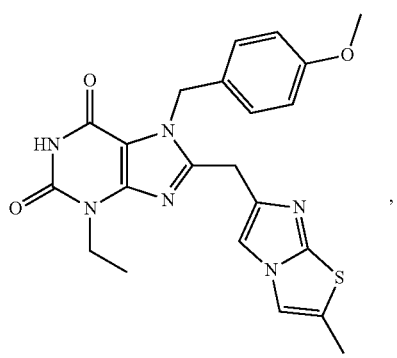
(I-28) 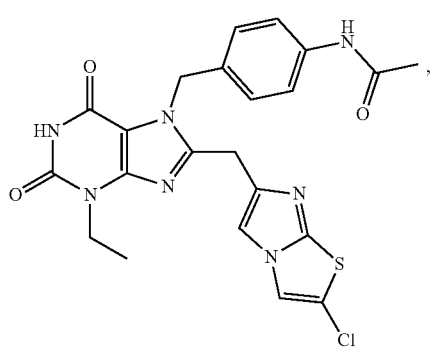
(I-29) 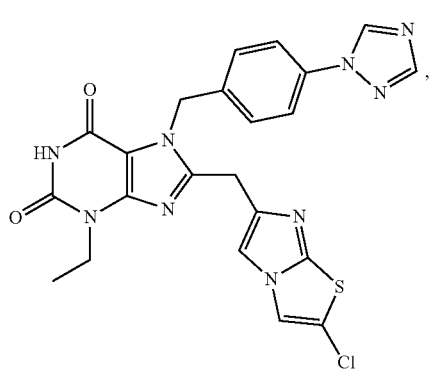
(I-30) 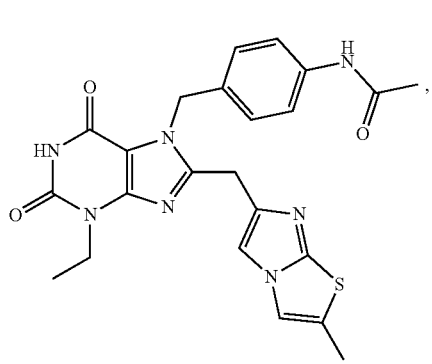

-continued
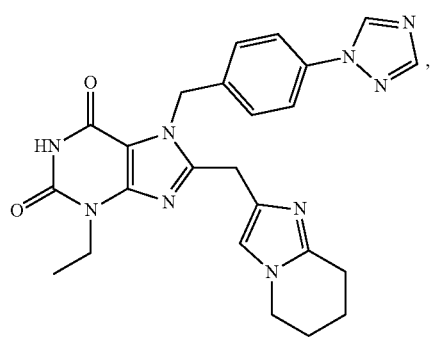 (I-31)
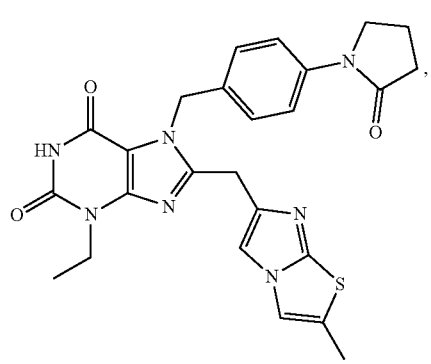 (I-32)
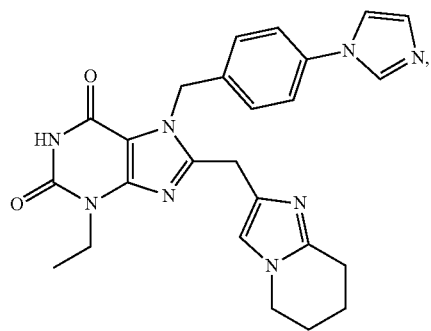 (I-33)
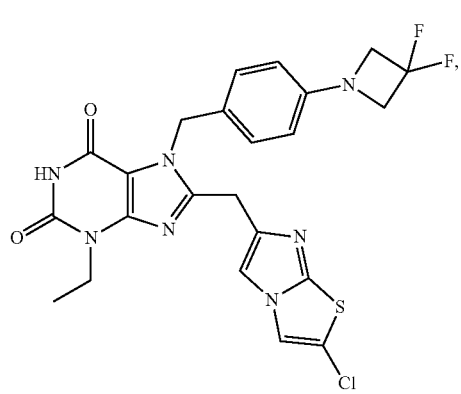 (I-34)
-continued
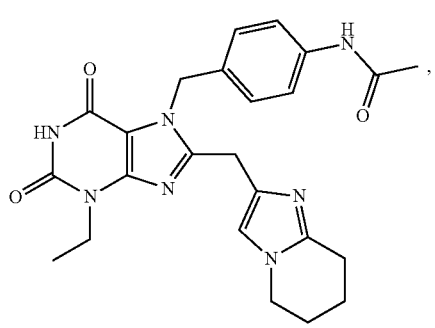 (I-35)
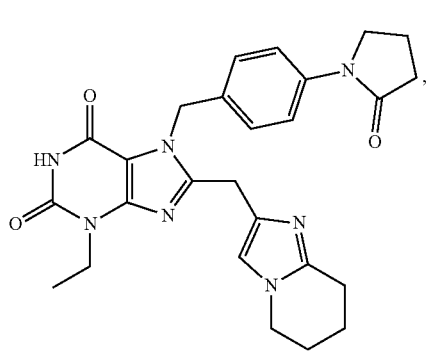 (I-36)
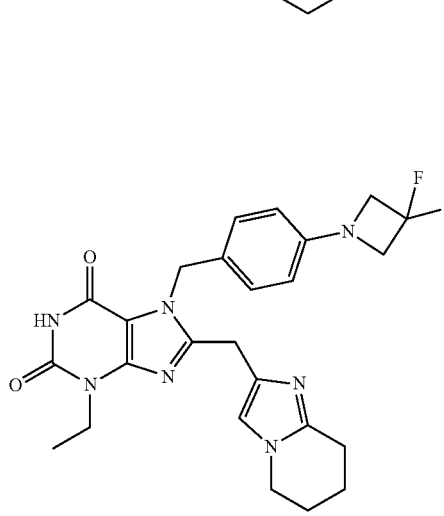 (I-37)
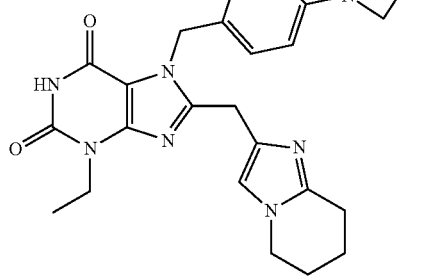 (I-38), and -continued
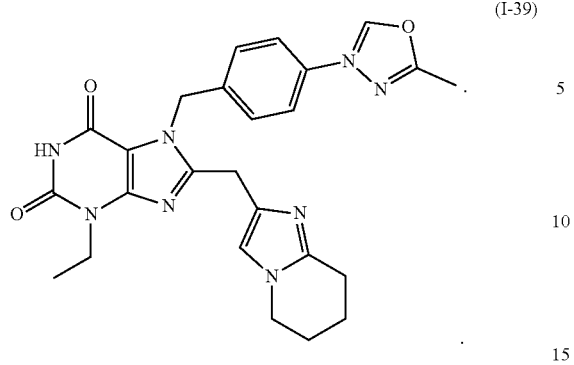
(I-39)
11. The method according to claim 1, wherein the compound or a pharmaceutically acceptable salt thereof is disposed in a medicament.
* * * * *